United States Patent
Hecht et al.

(10) Patent No.: US 9,440,967 B2
(45) Date of Patent: Sep. 13, 2016

(54) 1H-PYRROLO [2, 3 -B] PYRIDINE DERIVATIVES AND THEIR USE AS RADICAL QUENCHERS

(71) Applicants: Sidney Hecht, Phoenix, AZ (US);
Xiaoqing Cai, San Diego, CA (US);
Omar Khdour, Phoenix, AZ (US);
Jose I. Armendariz Guajardo,
Scottsdale, AZ (US)

(72) Inventors: Sidney Hecht, Phoenix, AZ (US);
Xiaoqing Cai, San Diego, CA (US);
Omar Khdour, Phoenix, AZ (US);
Jose I. Armendariz Guajardo,
Scottsdale, AZ (US)

(73) Assignee: Arizona Board of Regents on Behalf of Arizona State University,
Scottsdale, AZ (US)

( * ) Notice: Subject to any disclaimer, the term of this patent is extended or adjusted under 35 U.S.C. 154(b) by 0 days.

(21) Appl. No.: 14/371,579

(22) PCT Filed: Feb. 11, 2013

(86) PCT No.: PCT/US2013/025590
§ 371 (c)(1),
(2) Date: Jul. 10, 2014

(87) PCT Pub. No.: WO2013/120081
PCT Pub. Date: Aug. 15, 2013

(65) Prior Publication Data
US 2015/0011580 A1    Jan. 8, 2015

Related U.S. Application Data

(60) Provisional application No. 61/597,543, filed on Feb. 10, 2012.

(51) Int. Cl.
*C07D 471/04*    (2006.01)
(52) U.S. Cl.
CPC .................................. *C07D 471/04* (2013.01)
(58) Field of Classification Search
CPC .................................................... C07D 471/04
See application file for complete search history.

(56) References Cited

U.S. PATENT DOCUMENTS 3,476,772 A * 11/1969 Hoyle, Jr. et al. ............ 549/408
4,054,580 A * 10/1977 Ohi ................................ 549/411
8,952,025 B2 * 2/2015 Hecht et al. ................... 514/269

FOREIGN PATENT DOCUMENTS

DE           2315349      * 10/1974
WO   WO2011103536 A1    8/2011

OTHER PUBLICATIONS

James et al., (2005). "Interactions of mitochondria-targeted and untargeted ubiquinones with the mitochondrial respiratory chain and reactive oxygen species. Implications for the use of exogenous ubiquinones as therapies and experimental tools." J Biol. Chem. 280: 21295-21312.
Yin, (1996). "Biochemical basis of lipofuscin, ceroid, and age pigment-like fluorophores." Free Rad. Biol. Med. 21: 871-888.
Yamada et al., (2001). "Immunochemical detection of a lipofuscin-like fluorophore derived from malondialdehyde and lysine." J. Lipid Res. 42: 1187-1196.
Kuypers et al., (1987). "Parinaric acid as a sensitive fluorescent probe for the determination of lipid peroxidation." Biochim Biophys Acta. 921: 266-274.
McBride et al., (1986). "Nucleotide chemistry. 16. Amidine protecting groups for oligonucleotide synthesis." J. Am. Chem. Soc. 108: 2040-2048.
Yoon et al., (2003). "Iron-Sulfur Cluster Biosynthesis. Characterization of Frataxin as an Iron Donor for Assembly of [2Fe—2S] Clusters in ISU-Type Proteins." J. Am Chem. Soc. 125: 6078-6084.
Lu et al., (2010). "Concise synthesis of Bicyclic Pyridinol Antioxidants." Org. Lett. 12: 5189-5191.
Burton et al., (1986). "Vitamin E: application of the principles of physical organic chemistry to the exploration of its structure and function." Chem. Res. 19: 194-201.
Lamarche et al., (1980). "The cardiomyopathy of Friedreich's ataxia morphological observations in 3 cases." Can. J. Neurol. Sci. 7: 389-396.
Altman et al., (1993). "Comparison of Trypan Blue Dye Exclusion and Fluorometric Assays for Mammalian Cell Viability Determinations." Biotechnol. Prog. 9: 671-674.
Pratt et al., (2001). "5-Pyrimidinols: novel chain-breaking antioxidants more effective than phenols." J. Am. Chem. Soc. 123: 4625-4626.
International Search Report for PCT/US2013/025590, mailed May 6, 2013.
Chance et al., (1979). "Hydroperoxide Metabolism in Mammalian Organs." American Physiological Society 59(3): 527-605.
Stadtman, (2006). "Protein Oxidation and Aging." Free Radical Research 40(12): 1250-1258.
Droge, (2002). "Free Radicals in the Physiological Control of Cell Function." Physiol. Rev. 82: 47-95.

(Continued)

*Primary Examiner* — David K. O'Dell
(74) *Attorney, Agent, or Firm* — Viksnins Harris & Padys PLLP

(57) ABSTRACT

The present disclosure provides biologically active compounds of formula (I): and pharmaceutically acceptable salts thereof, compositions comprising these compounds, and methods of using these compounds in a variety of applications, such as treatment or suppression of diseases associated with decreased mitochondrial function resulting in diminished ATP production and/or oxidative stress and/or lipid peroxidation.

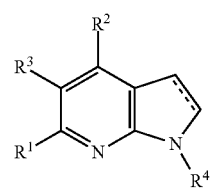

(I)

21 Claims, 4 Drawing Sheets

(56) References Cited

OTHER PUBLICATIONS

Valko et al., (2007). "Free radicals and antioxidants in normal physiological functions and human disease." Int. J. Biochem. Cell Biol. 39: 44-84.
Finkel, (2003). "Oxidant signals and oxidative stress." Curr. Opin. Chem. Biol. 15: 247-254.
Finkel et al., (2007). "The common biology of cancer and ageing." Nature 448: 767-774.
Barnham et al., (2004). "Neurodegenerative diseases and oxidative stress." Nat. Rev. Drug Discov. 3: 205-214.
Kirkinezos et al., (2001). "Reactive oxygen species and mitochondrial diseases." Cell & Developmental Biology 12: 449-457.
Zhang et al., (1990). "The oxidative inactivation of mitochondiral electron transport chain components and ATPase." Biol. Chem. 265: 16330-16336.
Wijtmans et al., (2003). "6-Amino-3-Pyridinols: Towards Diffusion-Controlled Chain-Breaking Antioxidants." Angew. Chem. Int. Ed. 42: 4370-4373.
Wijtmans et al., (2004). "Synthesis and Reactivity of Some 6-Substituted-2,4-dimethyl-3-pyridinols, a Novel Class of Chain-Breaking Antioxidants." Org. Chem. 69: 9215-9223.
Nam et al., (2007). "Tetrahydro-1,8-naphthyridinol Analogues of α-Tocopherol as Antioxidants in Lipid Membranes and Low-Density Lipoproteins." J. Am. Chem. Soc. 129: 10211-10219.
Serwa et al., (2010). "Preparation and Investigation of Vitamin B6-Derived Aminopyridinol Antioxidants." Chem. Eur. J. 16: 14106-14114.
Nam et al., (2011). "New synthetic route to N-tocopherol derivatives: synthesis of pyrrolopyridinol analogue of a-tocopherol from pyridoxine." Org. Biomol. Chem. 9, 1749-1755.
Lu et al., (2010). "Design, synthesis, and evaluation of an α-tocopherol analogue as a mitochondrial antioxidant." Bioorg. Med. Chem. 18: 7628-7638.
Khdour et al., (2011). "An acetate prodrug of a pyridinol-based vitamin E analogue." Pharm. Res. 28: 2896-2909.
Niki et al., (1985). "Effect of phytyl side chain of vitamin E on its antioxidant activity." J. Biol. Chem. 260: 2191-2196.
Constantinides et al., (2004). "Tocol emulsions for drug solubilization and parenteral delivery." Adv. Drug Deliv. Rev. 56: 1243-1255.
Burton et al., (1984). "beta-Carotene: an unusual type of lipid antioxidant." Science 224: 569-573.
Murase et al., (1998)."Antioxidant activity of a novel vitamin e derivative, 2-(a-d-glucopyranosyl)methyl-2,5,7,8-tetramethylchroman-6-ol." Free Radic. Biol. Med. 24: 217-225.
Valgimigli et al., (2003). "The Effect of Ring Nitrogen Atoms on the Homolytic Reactivity of Phenolic Compounds: Understanding the Radical-Scavenging Ability of 5-Pyrimidinols." Chem. Eur. J. 9: 4997-5010.
Gao et al., (2004). "A Convenient and Effective Method for Synthesizing β—Amino—α,β—Unsaturated Esters and Ketones." Synthetic Communications: An International Journal for Rapid Communication of Synthetic Organic Chemistry 34: 909-916.
Ingold et al., (1986). "A new vitamin E analogue more active than α-tocopherol in the rat curative myopathy bioassay." FEBS Lett. 205: 117-120.
Iuiliano et al., (1999). "Protection of low density lipoprotein oxidation by the antioxidant agent IRFI005, a new synthetic hydrophilic vitamin E analogue." Free Rad. Biol. Med. 26: 858-868.
Manfredini et al., (2000). "Novel antioxidant agents deriving from molecular combinations of vitamins C and E analogues: 3,4-dihydroxy-5(R)-[2(R,S)-(6-hydroxy-2,5,7,8-tetramethyl-chroman-2(R,S)-yl-methyl)-[1,3]dioxolan-4(S)-yl]-5H-furan-2-one and 3-O-octadecyl derivatives." Bioorg. Med. Chem. 8: 2791-2801.
Palozza et al., (2008). "Design, synthesis, and antioxidant potency of novel alpha-tocopherol analogues in isolated membranes and intact cells." Free Rad. Biol. Med. 44: 1452-1464.
Chua et al., (2005). "Oltipraz-induced phase 2 enzyme response conserved in cells lacking mitochondrial DNA." Biophys. Res. Commun. 337: 375-381.
Lu et al., (2007). "Role of calcium and cyclophilin D in the regulation of mitochondrial permeabilization induced by glutathione depletion." Biochem. Biophys. Res. Commun. 363: 572-577.
Zhang et al., (2008). "The Mitochondrial Permeability Transition Regulates Cytochrome c Release for Apoptosis during Endoplasmic Reticulum Stress by Remodeling the Cristae Junction." J. Biol. Chem. 283: 3476-3486.
Tirmenstein et al., (2000). "Glutathione depletion and the production of reactive oxygen species in isolated hepatocyte suspensions." Chem. Biol. Interact. 127: 201-217.
Lebel et al., (1992). "Evaluation of the probe 2',7'-dichlorofluorescin as an indicator of reactive oxygen species formation and oxidative stress." Chem. Res. Toxicol. 5: 227-231.
Pap et al., (1999). "Ratio-fuorescence microscopy of lipid oxidation in living cells using C11-BODIPY581/591." FEBS Lett. 453: 278-282.
Drummen et al., (2002). "C11-BODIPY581/591, an oxidation-sensitive fluorescent lipid peroxidation probe: (micro) spectroscopic characterization and validation of methodology." Free Rad. Biol. Med. 33: 473-490.
Bernardi et al., (2001). "A mitochondrial perspective on cell death." Trends Biochem. Sci. 26: 112-117.
Arce et al., (2011). "A Strategy for Suppressing Redox Stress within Mitochondria." ACS Med. Chem. Lett. 2: 608-613.
Ehrenberg et al., (1988). "Membrane potential can be determined in individual cells from the nernstian distribution of cationic dyes." Biophys. J. 53: 785-794.
Nam et al., (2011). "Pyridoxine-derived bicyclic aminopyridinol antioxidants: synthesis and their antioxidant activities." Organic and Biomolecular Chemistry 9(24): 8475-8482.
Cai et al., (2012). "Simplified bicyclic pyridinol analogues protect mitochondrial function." Bioorganic & Medicinal Chemistry 20(11): 3584-3595.
Dimauro et al., (2001). "Mitochondrial DNA mutations in human disease." Am. J. Med. Genet. 106: 18-26.
Leonard et al., (2000). "Mitochondrial respiratory chain disorders I: mitochondrial DNA defects." Lancet 355: 299-304.
Wilson et al., (1997). "Respiratory deficiency due to loss of mitochondrial DNA in yeast lacking the frataxin homologue." Nat. Genet. 16: 352-357.
Wilson, (2003). "Frataxin and frataxin deficiency in Friedreich's ataxia." J. Neural. Sci. 207: 103-105.
Campuzano et al., (1996). "Friedreich's ataxia: autosomal recessive disease caused by an intronic GAA triplet repeat expansion." Science 271: 1423-1427.
Campuzano et al., (1997). "Frataxin is reduced in Friedreich ataxia patients and is associated with mitochondrial membranes." Hum. Mol. Genet. 6: 1771-1780.
Bencze et al., (2007). "Human Frataxin: Iron and Ferrochelatase Binding" J. C.S. Chem. Commun. 18: 1798-1800.
Park et al., (2003). "Yeast frataxin sequentially chaperones and stores iron by coupling protein assembly with iron oxidation." J. Biol. Chem. 278: 31340-31351.
Yoon et al., (2004). "Frataxin-mediated iron delivery to ferrochelatase in the final step of heme biosynthesis." J. Biol. Chem. 279: 25943-25946.
Bulteau et al., (2004). "Frataxin Acts as an Iron Chaperone Protein to Modulate Mitochondrial Aconitase Activity." Science 305: 242-245.
Gonzalez-Cabo et al., (2005). "Frataxin interacts functionally with mitochondrial electron transport chain proteins." Hum. Mol. Genet. 14: 2091-2098.
Bradley et al., (2000). "Clinical, biochemical and molecular genetic correlations in Friedreich's ataxia." Hum. Mol. Genet. 9: 275-282.

* cited by examiner

1H-PYRROLO [2, 3 -B] PYRIDINE DERIVATIVES AND THEIR USE AS RADICAL QUENCHERS

CROSS-REFERENCE TO RELATED APPLICATIONS

This application is a U.S. National Phase of International Application No. PCT/US2013/025590, filed Feb. 11, 2013, which claims priority to U.S. Provisional Application No. 61/597,543, filed Feb. 10, 2012, the disclosures of which are hereby incorporated by reference in their entireties.

FIELD OF THE INVENTION

The present disclosure provides biologically active compounds multifunctional radical quenchers of formula (I) and pharmaceutically acceptable salts thereof, compositions comprising these compounds, and methods of using these compounds in a variety of applications, such as treatment or suppression of diseases associated with decreased mitochondrial function resulting in diminished ATP production and/or oxidative stress and/or lipid peroxidation.

SUMMARY OF THE INVENTION

Mitochondria are intracellular organelles responsible for a number of metabolic transformations and regulatory functions. They produce much of the ATP employed by eukaryotic cells. They are also the major source of free radicals and reactive oxygen species that cause oxidative stress. Consequently, mitochondrial defects are damaging, particularly to neural and muscle tissues which have high energy level demands. Thus, energetic defects have been implicated in forms of movement disorders, cardiomyopathy, myopathy, blindness, and deafness (DiMauro et al. (2001) *Am. J. Med. Genet.* 106, 18-26; Leonard et al. (2000) *Lancet.* 355, 299-304). There are a number of mitochondrial diseases resulting from both nuclear and mitochondrial genetic defects, and the underlying biochemistries of these diseases tend to be rather similar. They include increased lactate production, diminished respiration and ATP production, and reflect the consequences of oxidative stress. This invention describes novel compounds for the treatment or suppression of diseases associated with decreased mitochondrial function resulting in diminished ATP production and/or oxidative stress and/or lipid peroxidation. The invention also describes use of these compounds for the treatment of mitochondrial disorders, including but not limited to Friedreich's ataxia, Leber's Hereditary Optic Neuropathy, Kearns-Sayre Syndrome, Mitochondrial Encephalomyopathy with Lactic Acidosis and Stroke-Like Episodes and more generally, any disease associated with impairment of energy production and mitochondrial function.

Thus, in one aspect, the disclosure provides compounds of formula (I):

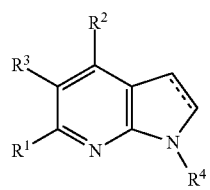

(I)

or a pharmaceutically acceptable salt thereof, wherein bond "----" is a single or a double bond;
$R^1$ is $C_4$-$C_{20}$ alkyl, $C_4$-$C_{20}$ alkenyl, or $C_4$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, —$CON(R^5)_2$, cycloalkyl, aryl, heteroaryl, and heterocycle, wherein each cycloalkyl, aryl, heteroaryl, and heterocycle are optionally substituted with $R^9$;
where each $R^5$ independently is hydrogen, $C_1$-$C_6$ alkyl, halo($C_1$-$C_6$ alkyl), cycloalkyl, aryl, heteroaryl, or heterocycle;
wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;
$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$; where each $R^6$ independently is hydrogen or $C_1$-$C_6$ alkyl;
$R^3$ is hydrogen, halogen, $C_1$-$C_6$ alkyl, $C_2$-$C_6$ alkenyl, $C_2$-$C_6$ alkynyl, or —$OR^7$, where $R^7$ is hydrogen, $C_1$-$C_6$ alkyl, halo($C_1$-$C_6$ alkyl), or —$CO(C_1$-$C_6$ alkyl); and
$R^4$ is hydrogen, $C_1$-$C_6$ alkyl, $C_2$-$C_6$ alkenyl, $C_2$-$C_6$ alkynyl, $C_3$-$C_8$ cycloalkyl($C_1$-$C_6$ aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^7$,
wherein each $R^8$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

Another aspect of the disclosure provides pharmaceutical compositions comprising the compounds and salts of the disclosure and an appropriate carrier, excipient or diluent. The exact nature of the carrier, excipient or diluent will depend upon the desired use for the composition, and may range from being suitable for veterinary uses to being suitable for human use. The compositions may optionally include one or more additional compounds suitable for a use.

Another aspect of the disclosure provides methods of treating or suppressing diseases associated with decreased mitochondrial function resulting in diminished ATP production and/or oxidative stress and/or lipid peroxidation, comprising administering an effective amount of the compound and salts of the disclosure.

Another aspect of the disclosure provides a method of treating or suppressing one or more of Friedreich's ataxia, Leber's Hereditary Optic Neuropathy, Kearns-Sayre Syndrome, Mitochondrial Encephalomyopathy with Lactic Acidosis and Stroke-Like Episodes, or Leigh syndrome, comprising administering an effective amount of the compound and salts of the disclosure.

Another aspect of the disclosure provides a method of treating or suppressing one or more of obesity, atherosclerosis, Parkinson's Disease, cancer, heart failure, myocardial infarction (MI), Alzheimer's Disease, Huntington's Disease, schizophrenia, bipolar disorder, fragile X syndrome, chronic fatigue syndrome, and Leigh syndrome, comprising administering an effective amount of the compound and salts of the disclosure.

The compounds of the invention, increase ATP concentration in $CoQ_{10}$ deficient cells. In addition, the compounds of the invention inhibit lipid peroxidation and prevent reactive oxygen species (ROS) production in cells depleted of the antioxidant glutathione (GSH) using the chemical diethyl maleate. Moreover, these compounds all prevented ROS-dependent cell death after the cells were depleted of GSH. The antioxidant potential of the compounds described above is significantly increased compared to that of α-tocopherol (α-TOH) and idebenone; therefore, these compounds have the potential of improved efficacy in clinical applications compared to α-tocopherol and idebenone.

DETAILED DESCRIPTION OF THE INVENTION

Figure 1:
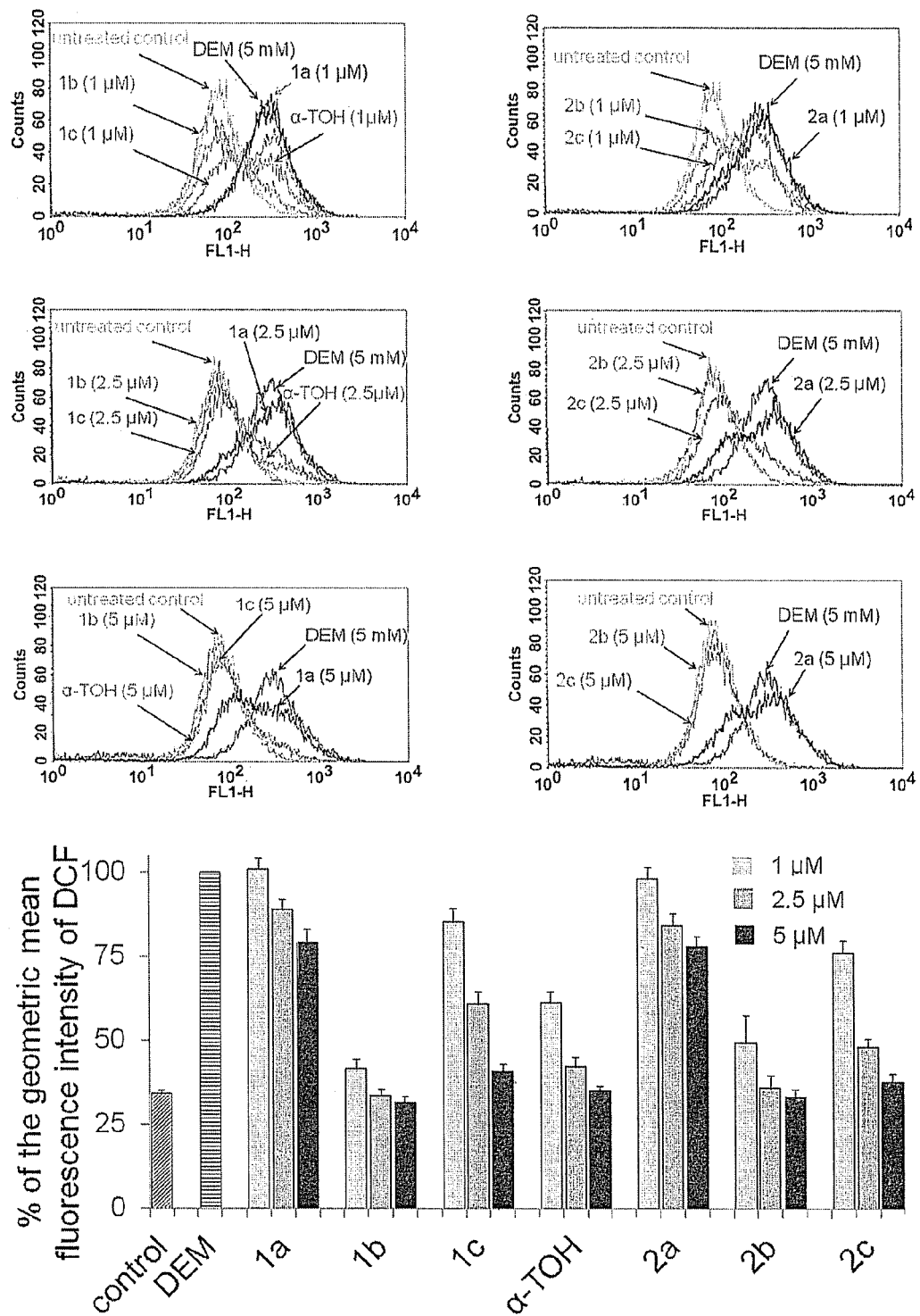
FIG. 1. Representative flow cytometric histograms overlay showing ROS production in CEM cells. Following pretreatment with the indicated compounds (1, 2.5 and 5 μM) for 16 h, the cells were treated with 5 mM diethyl maleate (DEM) for 50 min to deplete glutathione. The cells were washed in phosphate-buffered saline, and suspended in phosphate-buffered saline containing 20 mM glucose. Cells were loaded with 10 μM dichlorodihydrofluoresceindiacetate (DCFH-DA) for 20 min, and the green fluorescence (DCF) was measured by flow cytometry using the FL1-H channel. The figure shows a representative example of three independent experiments. A total of 10000 events were recorded for each sample and analyzed with the CellQuest software (BD Biosciences). Increased DCF fluorescence, a measure of intracellular oxidation and ROS production, was determined by a shift in DCF fluorescence to the right on the x-axis of the FACS histogram. The bottom panel shows a bar graph of the percentage of the geometric mean fluorescence intensity (GMFI) of DCF fluorescence relative to a DEM-treated control. Data are expressed as the mean±SEM (n=3). α-TOH is α-tocopherol.

In one aspect, the disclosure provides compounds of formula (I):

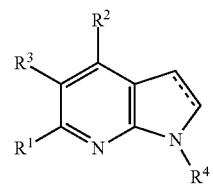

(I)

or a pharmaceutically acceptable salt thereof, wherein bond " ---- " is a single or a double bond;

$R^1$ is $C_4$-$C_{20}$ alkyl, $C_4$-$C_{20}$ alkenyl, or $C_4$-$C_{20}$ alkynyl, each optionally substituted with one to four substituents selected from halogen, cyano, nitro, $C_1$-$C_6$ alkyl, halo($C_1$-$C_6$ alkyl), —OR$^5$, —NR$^5{}_2$, —CO$_2$R$^5$, —CON(R$^5$)$_2$, cycloalkyl, aryl, heteroaryl, and heterocycle, wherein each cycloalkyl, aryl, heteroaryl, and heterocycle are optionally substituted with $R^9$;

where each $R^5$ independently is hydrogen, $C_1$-$C_6$ alkyl, halo($C_1$-$C_6$ alkyl), cycloalkyl, aryl, heteroaryl, or heterocycle;

wherein each $R^9$ independently is halogen, cyano, nitro, —N$_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —OR$^6$, —NR$^6{}_2$, —CO$_2$R$^6$, and —CONR$^6{}_2$; where each $R^6$ independently is hydrogen or $C_1$-$C_6$ alkyl;

$R^3$ is hydrogen, halogen, $C_1$-$C_6$ alkyl, $C_2$-$C_6$ alkenyl, $C_2$-$C_6$ alkynyl, or —OR$^7$, where $R^7$ is hydrogen, $C_1$-$C_6$ alkyl, halo($C_1$-$C_6$ alkyl), or —CO($C_1$-$C_6$ alkyl); and $R^4$ is hydrogen, $C_1$-$C_6$ alkyl, $C_2$-$C_6$ alkenyl, $C_2$-$C_6$ alkynyl, $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^7$, wherein each $R^8$ independently is halogen, cyano, nitro, —N$_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In one embodiment, the disclosure provides compounds of formula (I), which are of formula (II):

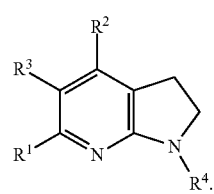

(II)

In one embodiment, the disclosure provides compounds of formula (I), which are of formula (III):

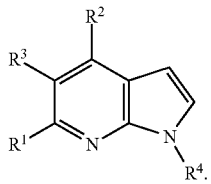

(III)

In another embodiment, the disclosure provides compounds of formulae (I)-(III), wherein $R^4$ is hydrogen or $C_1$-$C_6$ alkyl. In another embodiment, $R^4$ is hydrogen or $C_1$-$C_3$ alkyl.

In another embodiment, the disclosure provides compounds as described above with any reference to formulae (I)-(III), wherein $R^4$ is hydrogen.

In yet another embodiment, the disclosure provides compounds as described above with any reference to formulae (I)-(III), wherein $R^4$ is $C_1$-$C_3$ alkyl. In one embodiment, $R^4$ is methyl or ethyl. In yet another embodiment, $R^4$ is methyl.

In yet another embodiment, the disclosure provides compounds as described above with any reference to formulae (I)-(III), wherein $R^2$ is $C_1$-$C_4$ alkyl, optionally substituted with one to four substituents selected from halogen, cyano, nitro, $C_1$-$C_6$ alkyl, halo($C_1$-$C_6$ alkyl), —$OR^6$, —$NR^6{}_2$, —$CO_2R^6$, and —$CONR^6{}_2$; where each $R^6$ independently is hydrogen or $C_1$-$C_6$ alkyl.

In one embodiment, the disclosure provides compounds as described above with any reference to formulae (I)-(III), wherein $R^2$ is unsubstituted $C_1$-$C_4$ alkyl. In one embodiment, $R^2$ is unsubstituted $C_1$-$C_2$ alkyl. In another embodiment, $R^2$ is methyl or ethyl. In yet another embodiment, $R^2$ is methyl.

In one embodiment, the disclosure provides compounds as described above with any reference to formulae (I)-(III), wherein $R^3$ is hydrogen, halogen, $C_1$-$C_6$ alkyl, or —$OR^7$, where $R^7$ is hydrogen, $C_1$-$C_6$ alkyl, halo($C_1$-$C_6$ alkyl), or —$CO(C_1$-$C_6$ alkyl).

In another embodiment, the disclosure provides compounds as described above with any reference to formulae (I)-(III), wherein $R^3$ is hydrogen or halogen.

In yet another embodiment, the disclosure provides compounds as described above with any reference to formulae (I)-(III), wherein $R^3$ is hydrogen.

In yet another embodiment, the disclosure provides compounds as described above with any reference to formulae (I)-(III), wherein $R^3$ is halogen.

In one embodiment, the disclosure provides compounds as described above with any reference to formulae (I)-(III), wherein $R^3$ is $C_1$-$C_6$ alkyl, or —$OR^7$, where $R^7$ is hydrogen, $C_1$-$C_6$ alkyl, halo($C_1$-$C_6$ alkyl), or —$CO(C_1$-$C_6$ alkyl).

In another embodiment, the disclosure provides compounds as described above with any reference to formulae (I)-(III), wherein $R^3$ is $C_1$-$C_6$ alkyl.

In another embodiment, the disclosure provides compounds as described above with any reference to formulae (I)-(III), wherein $R^3$ is —$OR^7$, where $R^7$ is hydrogen, $C_1$-$C_6$ alkyl, halo($C_1$-$C_6$ alkyl), or —$CO(C_1$-$C_6$ alkyl). Another embodiment provides compounds where $R^3$ is —$OR^7$, where $R^7$ is hydrogen, $C_1$-$C_6$ alkyl, or —$CO(C_1$-$C_6$ alkyl). In another embodiment, $R^3$ is —OH. In another embodiment, $R^3$ is —$O(CH_3)$.

In one embodiment, the disclosure provides compounds as described above with any reference to formulae (I)-(III), wherein $R^3$ is —$OCO(C_1$-$C_6$ alkyl). Another embodiment provides compounds where $R^3$ is —$OCOCH_3$.

In one embodiment, the disclosure provides compounds a described above with any reference to formulae (I)-(III), wherein $R^1$ is $C_4$-$C_{20}$ alkyl, $C_4$-$C_{20}$ alkenyl, or $C_4$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5{}_2$, —$CO_2R^5$, and —CON($R^5$)$_2$; where each $R^5$ independently is hydrogen, $C_1$-$C_6$ alkyl, halo($C_1$-$C_6$ alkyl), cycloalkyl, aryl, heteroaryl, or heterocycle.

In one embodiment, the disclosure provides compounds as described above with any reference to formulae (I)-(III), wherein $R^1$ is $C_4$-$C_{20}$ alkyl, $C_4$-$C_{20}$ alkenyl, or $C_4$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5{}_2$, —$CO_2R^5$, and —CON($R^5$)$_2$; where each $R^5$ independently is hydrogen, $C_1$-$C_6$ alkyl, or halo($C_1$-$C_6$ alkyl).

In one embodiment, the disclosure provides compounds as described above with any reference to formulae (I)-(III), wherein $R^1$ is $C_4$-$C_{20}$ alkyl, optionally substituted with one to four substituents selected from halogen, cyano, nitro, $C_1$-$C_6$ alkyl, halo($C_1$-$C_6$ alkyl), —$OR^5$, —$NR^5{}_2$, —$CO_2R^5$, —CON($R^5$)$_2$, cycloalkyl, aryl, heteroaryl, and heterocycle, wherein each cycloalkyl, aryl, heteroaryl, and heterocycle are optionally substituted with $R^9$; where each $R^5$ independently is hydrogen, $C_1$-$C_6$ alkyl, halo($C_1$-$C_6$ alkyl), cycloalkyl, aryl, heteroaryl, or heterocycle; and wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In one embodiment, the disclosure provides compounds as described above with any reference to formulae (I)-(III), wherein $R^1$ is $C_4$-$C_{20}$ alkyl, optionally substituted with one to four substituents selected from halogen, cyano, nitro, $C_1$-$C_6$ alkyl, halo($C_1$-$C_6$ alkyl), —$OR^5$, —$NR^5{}_2$, —$CO_2R^5$, —CON($R^5$)$_2$, cycloalkyl, aryl, heteroaryl, and heterocycle, wherein each cycloalkyl, aryl, heteroaryl, and heterocycle are optionally substituted with $R^9$; where each $R^5$ independently is hydrogen, $C_1$-$C_6$ alkyl, or halo($C_1$-$C_6$ alkyl); and wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$allylamino.

In one embodiment, the disclosure provides compounds as described above with any reference to formulae (I)-(III), wherein $R^1$ is $C_4$-$C_{20}$ alkyl, optionally substituted with one to four substituents selected from halogen, cyano, nitro, $C_1$-$C_6$ alkyl, halo($C_1$-$C_6$ alkyl), —$OR^5$, —$NR^5{}_2$, —$CO_2R^5$, and —CON($R^5$)$_2$; where each $R^5$ independently is hydrogen, $C_1$-$C_6$ alkyl, or halo($C_1$-$C_6$ alkyl).

In another embodiment, the disclosure provides compounds as described above with any reference to formulae (I)-(III), wherein $R^1$ is $C_4$-$C_{20}$ alkyl, optionally substituted with one to four substituents selected from halogen, $C_1$-$C_6$ alkyl, halo($C_1$-$C_6$ alkyl), —$OR^5$, —$NR^5{}_2$, —$CO_2R^5$, and —CON($R^5$)$_2$; where each $R^5$ independently is hydrogen, $C_1$-$C_6$ alkyl, or halo($C_1$-$C_6$ allyl). In yet another embodiment, $R^1$ is $C_4$-$C_{20}$ alkyl optionally substituted with one to four —OH groups.

In one embodiment, the disclosure provides compounds as described above with any reference to formulae (I)-(III), wherein $R^1$ is $C_5$-$C_{20}$ alkyl, optionally substituted with one to four substituents selected from halogen, cyano, nitro, $C_1$-$C_6$ alkyl, halo($C_1$-$C_6$ alkyl), —$OR^5$, —$NR^5{}_2$, —CON $(R^5)_2$, cycloalkyl, aryl, heteroaryl, and heterocycle, wherein each cycloalkyl, aryl, heteroaryl, and heterocycle are optionally substituted with $R^9$; where each $R^5$ independently is hydrogen, $C_1$-$C_6$ alkyl, halo($C_1$-$C_6$ alkyl), cycloalkyl, aryl, heteroaryl, or heterocycle; and wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In one embodiment, the disclosure provides compounds as described above with any reference to formulae (I)-(III), wherein $R^1$ is $C_5$-$C_{20}$ alkyl, optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, —$CON(R^5)_2$, cycloalkyl, aryl, heteroaryl, and heterocycle, wherein each cycloalkyl, aryl, heteroaryl, and heterocycle are optionally substituted with $R^9$; where each $R^5$ independently is hydrogen, $C_1$-$C_6$ alkyl, or halo($C_1$-$C_6$ alkyl); and wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In one embodiment, the disclosure provides compounds as described above with any reference to formulae (I)-(III), wherein $R^1$ is $C_6$-$C_{20}$ alkyl, optionally substituted with one to four substituents selected from halogen, $C_1$-$C_6$ alkyl, halo($C_1$-$C_6$ alkyl), —$OR^5$, —$NR^5_2$, —$CO_2R^5$, and —$CON(R^5)_2$; where each $R^5$ independently is hydrogen, $C_1$-$C_6$ alkyl, or halo($C_1$-$C_6$ alkyl). Another embodiment provides compounds where $R^1$ is $C_5$-$C_{20}$ alkyl optionally substituted with one to four —OH groups.

In one embodiment, the disclosure provides compounds as described above with any reference to formulae (I)-(III), wherein $R^1$ is $C_6$-$C_{20}$ alkyl, optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, —$CON(R^5)_2$, cycloalkyl, aryl, heteroaryl, and heterocycle, wherein each cycloalkyl, aryl, heteroaryl, and heterocycle are optionally substituted with $R^9$; where each $R^5$ independently is hydrogen, $C_1$-$C_6$ alkyl, halo($C_1$-$C_6$ alkyl), cycloalkyl, aryl, heteroaryl, or heterocycle; and wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In one embodiment, the disclosure provides compounds as described above with any reference to formulae (I)-(III), wherein $R^1$ is $C_6$-$C_{20}$ alkyl, optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, —$CON(R^5)_2$, cycloalkyl, aryl, heteroaryl, and heterocycle, wherein each cycloalkyl, aryl, heteroaryl, and heterocycle are optionally substituted with $R^9$; where each $R^5$ independently is hydrogen, $C_1$-$C_6$ alkyl, or halo($C_1$-$C_6$ alkyl); and wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In one embodiment, the disclosure provides compounds as described above with any reference to formulae (I)-(III), wherein $R^1$ is $C_6$-$C_{20}$ alkyl, optionally substituted with one to four substituents selected from halogen, $C_1$-$C_6$ alkyl, halo($C_1$-$C_6$ alkyl), —$OR^5$, —$NR^5_2$, —$CO_2R^5$, and —$CON(R^5)_2$; where each $R^5$ independently is hydrogen, $C_1$-$C_6$ alkyl, or halo($C_1$-$C_6$ alkyl). Another embodiment provides compounds where $R^1$ is $C_6$-$C_{20}$ alkyl optionally substituted with one to four —OH groups.

In one embodiment, the disclosure provides compounds as described above with any reference to formulae (I)-(III), wherein $R^1$ is $C_7$-$C_{20}$ alkyl, optionally substituted with one to four substituents selected from halogen, cyano, nitro, $C_1$-$C_6$ alkyl, halo($C_1$-$C_6$ alkyl), —$OR^5$, —$CO_2R^5$, —$CON(R^5)_2$, cycloalkyl, aryl, heteroaryl, and heterocycle, wherein each cycloalkyl, aryl, heteroaryl, and heterocycle are optionally substituted with $R^9$; where each $R^5$ independently is hydrogen, $C_1$-$C_6$ alkyl, halo($C_1$-$C_6$ alkyl), cycloalkyl, aryl, heteroaryl, or heterocycle; and wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In one embodiment, the disclosure provides compounds as described above with any reference to formulae (I)-(III), wherein $R^1$ is $C_7$-$C_{20}$ alkyl, optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, —$CON(R^5)_2$, cycloalkyl, aryl, heteroaryl, and heterocycle, wherein each cycloalkyl, aryl, heteroaryl, and heterocycle are optionally substituted with $R^9$; where each $R^5$ independently is hydrogen, $C_1$-$C_6$ alkyl, or halo($C_1$-$C_6$ alkyl); and wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In one embodiment, the disclosure provides compounds as described above with any reference to formulae (I)-(III), wherein $R^1$ is $C_7$-$C_{20}$ alkyl, optionally substituted with one to four substituents selected from halogen, $C_1$-$C_6$ alkyl, halo($C_1$-$C_6$ alkyl), —$OR^5$, —$NR^5_2$, —$CO_2R^5$, and —$CON(R^5)_2$; where each $R^5$ independently is hydrogen, $C_1$-$C_6$ alkyl, or halo($C_1$-$C_6$ alkyl). Another embodiment provides compounds where $R^1$ is $C_7$-$C_{20}$ alkyl optionally substituted with one to four —OH groups.

In another embodiment, the disclosure provides compounds as described above with any reference to formulae (I)-(III), wherein $R^1$ is unsubstituted $C_4$-$C_{20}$ alkyl. In yet another embodiment, the disclosure provides compounds as described above with any reference to formulae (I)-(III), wherein $R^1$ is unsubstituted $C_5$-$C_{20}$ alkyl. In yet another embodiment, the disclosure provides compounds as described above with any reference to formulae (I)-(III), wherein $R^1$ is unsubstituted $C_6$-$C_{20}$ alkyl.

In yet another embodiment, the disclosure provides compounds as described above with any reference to formulae (I)-(III), wherein $R^1$ is unsubstituted $C_7$-$C_{20}$ alkyl.

In another embodiment, the disclosure provides compounds as described above with any reference to formulae (I)-(III), wherein $R^1$ is straight-chain unsubstituted alkyl. In this embodiment, the straight-chain unsubstituted alkyl having 4-20 carbon atoms, or 5-20 carbon atoms, or 6-20 carbon atoms, or 7-20 carbon atoms.

In yet another embodiment, the disclosure provides compounds as described above with any reference to formulae (I)-(III), wherein $R^1$ is pentyl, decyl or hexadecyl.

In one embodiment, the disclosure provides compounds as described above with any reference to formulae (I)-(III), wherein
$R^1$ is $C_4$-$C_{20}$ alkyl, $C_4$-$C_{20}$ alkenyl, or $C_4$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, —$CON(R^5)_2$, cycloalkyl, aryl, heteroaryl, and heterocycle,
wherein each cycloalkyl, aryl, heteroaryl, and heterocycle are optionally substituted with $R^9$;
where each $R^5$ independently is hydrogen, $C_1$-$C_6$ alkyl, or halo($C_1$-$C_6$ alkyl);
wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —OR$^6$, —NR$^6{}_2$, —CO$_2$R$^6$, and —CONR$^6{}_2$; where each R$^6$ independently is hydrogen or $C_1$-$C_6$ alkyl;

$R^3$ is $C_1$-$C_6$ alkyl or —OR$^7$, where R$^7$ is hydrogen, $C_1$-$C_6$ alkyl, halo($C_1$-$C_6$ alkyl), or —CO($C_1$-$C_6$ alkyl); and $R^4$ is hydrogen, or $C_1$-$C_6$ alkyl.

In one embodiment, the disclosure provides compounds as described above with any reference to formulae (I)-(III), wherein $R^1$ is $C_4$-$C_{20}$ alkyl, $C_4$-$C_{20}$ alkenyl, or $C_4$-$C_{20}$ alkynyl, each optionally substituted with one to four substituents selected from halogen, cyano, nitro, $C_1$-$C_6$ alkyl, halo($C_1$-$C_6$ alkyl), —OR$^5$, —NR$^5{}_2$, —CO$_2$R$^5$, and —CON(R$^5$)$_2$; where each R$^5$ independently is hydrogen, $C_1$-$C_6$ alkyl, or halo($C_1$-$C_6$ alkyl);

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —OR$^6$, —NR$^6{}_2$, —CO$_2$R$^6$, and —CONR$^6{}_2$; where each R$^6$ independently is hydrogen or $C_1$-$C_6$ alkyl;

$R^3$ is $C_1$-$C_6$ alkyl or —OR$^7$, where R$^7$ is hydrogen, $C_1$-$C_6$ alkyl, halo($C_1$-$C_6$ alkyl), or —CO($C_1$-$C_6$ alkyl); and $R^4$ is hydrogen, or $C_1$-$C_6$ alkyl.

In one embodiment, the disclosure provides compounds as described above with any reference to formulae (I)-(III), wherein $R^1$ is $C_4$-$C_{20}$ alkyl, $C_4$-$C_{20}$ alkenyl, or $C_4$-$C_{20}$ alkynyl, each optionally substituted with one to four substituents selected from halogen, cyano, nitro, $C_1$-$C_6$ alkyl, halo($C_1$-$C_6$ alkyl), —OR$^5$, —NR$^5{}_2$, —CO$_2$R$^5$, and —CON(R$^5$)$_2$; where each R$^5$ independently is hydrogen, $C_1$-$C_6$ alkyl, or halo($C_1$-$C_6$ alkyl);

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —OR$^6$, —NR$^6{}_2$, —CO$_2$R$^6$, and —CONR$^6{}_2$; where each R$^6$ independently is hydrogen or $C_1$-$C_6$ alkyl;

$R^3$ is —OR$^7$, where R$^7$ is hydrogen, $C_1$-$C_6$ alkyl, halo($C_1$-$C_6$ alkyl), or —CO($C_1$-$C_6$ alkyl); and $R^4$ is hydrogen, or $C_1$-$C_6$ alkyl.

In another embodiment, the disclosure provides compounds as described above with any reference to formulae (I)-(III), wherein $R^1$ is $C_4$-$C_{20}$ alkyl, $C_4$-$C_{20}$ alkenyl, or $C_4$-$C_{20}$ alkynyl, each optionally substituted with one to four substituents selected from halogen, cyano, nitro, $C_1$-$C_6$ alkyl, halo($C_1$-$C_6$ alkyl), —OR$^5$, —NR$^5{}_2$, —CO$_2$R$^5$, and —CON(R$^5$)$_2$; where each R$^5$ independently is hydrogen, $C_1$-$C_6$ alkyl, or halo($C_1$-$C_6$ alkyl);

$R^2$ is $C_1$-$C_4$ alkyl, $C_2$-$C_4$ alkenyl, or $C_2$-$C_4$ alkynyl, each optionally substituted with one to four substituents selected from halogen, cyano, nitro, $C_1$-$C_6$ alkyl, halo($C_1$-$C_6$ alkyl), —OR$^6$, —NR$^6{}_2$, —CO$_2$R$^6$, and —CONR$^6{}_2$; where each R$^6$ independently is hydrogen or $C_1$-$C_6$ alkyl;

$R^3$ is —OR$^7$, where R$^7$ is hydrogen, $C_1$-$C_6$ alkyl, halo($C_1$-$C_6$ alkyl), or —CO($C_1$-$C_6$ alkyl); and $R^4$ is $C_1$-$C_6$ alkyl.

In one embodiment, the disclosure provides compounds as described above with any reference to formulae (I)-(III), wherein $R^1$ is $C_5$-$C_{20}$ alkyl, $C_5$-$C_{20}$ alkenyl, or $C_5$-$C_{20}$ alkynyl, each optionally substituted with one to four substituents selected from halogen, cyano, nitro, $C_1$-$C_6$ alkyl, halo($C_1$-$C_6$ alkyl), —OR$^5$, —NR$^5{}_2$, —CO$_2$R$^5$, —CON(R$^5$)$_2$, cycloalkyl, aryl, heteroaryl, and heterocycle, wherein each cycloalkyl, aryl, heteroaryl, and heterocycle are optionally substituted with R$^9$;

where each R$^5$ independently is hydrogen, $C_1$-$C_6$ alkyl, or halo($C_1$-$C_6$ alkyl);

wherein each R$^9$ independently is halogen, cyano, nitro, —N$_3$, $C_1$-$C_6$ alkyl, halo($C_1$-$C_6$ alkyl), $C_1$-$C_6$ alkoxy, amino, $C_1$-$C_6$alkylamino, or diC$_1$-C$_6$alkylamino;

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —OR$^6$, —NR$^6{}_2$, —CO$_2$R$^6$, and —CONR$^6{}_2$; where each R$^6$ independently is hydrogen or $C_1$-$C_6$ alkyl;

$R^3$ is $C_1$-$C_6$ alkyl or —OR$^7$, where R$^7$ is hydrogen, $C_1$-$C_6$ alkyl, halo($C_1$-$C_6$ alkyl), or —CO($C_1$-$C_6$ alkyl); and $R^4$ is hydrogen, or $C_1$-$C_6$ alkyl.

In one embodiment, the disclosure provides compounds as described above with any reference to formulae (I)-(III), wherein $R^1$ is $C_5$-$C_{20}$ alkyl, $C_5$-$C_{20}$ alkenyl, or $C_5$-$C_{20}$ alkynyl, each optionally substituted with one to four substituents selected from halogen, cyano, nitro, $C_1$-$C_6$ alkyl, halo($C_1$-$C_6$ alkyl), —OR$^5$, —NR$^5{}_2$, —CO$_2$R$^5$, and —CON(R$^5$)$_2$; where each R$^5$ independently is hydrogen, $C_1$-$C_6$ alkyl, or halo($C_1$-$C_6$ alkyl);

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —OR$^6$, —NR$^6{}_2$, —CO$_2$R$^6$, and —CONR$^6{}_2$; where each R$^6$ independently is hydrogen or $C_1$-$C_6$ alkyl;

$R^3$ is $C_1$-$C_6$ alkyl or —OR$^7$, where R$^7$ is hydrogen, $C_1$-$C_6$ alkyl, halo($C_1$-$C_6$ alkyl), or —CO($C_1$-$C_6$ alkyl); and $R^4$ is hydrogen, or $C_1$-$C_6$ alkyl.

In one embodiment, the disclosure provides compounds as described above with any reference to formulae (I)-(III), wherein $R^1$ is $C_5$-$C_{20}$ alkyl, $C_5$-$C_{20}$ alkenyl, or $C_5$-$C_{20}$ alkynyl, each optionally substituted with one to four substituents selected from halogen, cyano, nitro, $C_1$-$C_6$ alkyl, halo($C_1$-$C_6$ alkyl), —OR$^5$, —NR$^5{}_2$, —CO$_2$R$^5$, and —CON(R$^5$)$_2$; where each R$^5$ independently is hydrogen, $C_1$-$C_6$ alkyl, or halo($C_1$-$C_6$ alkyl);

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —OR$^6$, —NR$^6{}_2$, —CO$_2$R$^6$, and —CONR$^6{}_2$; where each R$^6$ independently is hydrogen or $C_1$-$C_6$ alkyl;

$R^3$ is —OR$^7$, where R$^7$ is hydrogen, $C_1$-$C_6$ alkyl, halo($C_1$-$C_6$ alkyl), or —CO($C_1$-$C_6$ alkyl); and $R^4$ is hydrogen, or $C_1$-$C_6$ alkyl.

In another embodiment, the disclosure provides compounds as described above with any reference to formulae (I)-(III), wherein $R^1$ is $C_5$-$C_{20}$ alkyl, $C_5$-$C_{20}$ alkenyl, or $C_5$-$C_{20}$ alkynyl, each optionally substituted with one to four substituents selected from halogen, cyano, nitro, $C_1$-$C_6$ alkyl, halo($C_1$-$C_6$ alkyl), —OR$^5$, —NR$^5{}_2$, —CO$_2$R$^5$, and —CON(R$^5$)$_2$; where each R$^5$ independently is hydrogen, $C_1$-$C_6$ alkyl, or halo($C_1$-$C_6$ alkyl);

$R^2$ is $C_1$-$C_4$ alkyl, $C_2$-$C_4$ alkenyl, or $C_2$-$C_4$ alkynyl, each optionally substituted with one to four substituents selected from halogen, cyano, nitro, $C_1$-$C_6$ alkyl, halo($C_1$-

$C_6$ alkyl), —$OR^6$, —$NR^6_2$, —$CO_2R^6$, and —$CONR^6_2$; where each $R^6$ independently is hydrogen or $C_1$-$C_6$ alkyl;

$R^3$ is —$OR^7$, where $R^7$ is hydrogen, $C_1$-$C_6$ alkyl, halo($C_1$-$C_6$ alkyl), or —$CO(C_1$-$C_6$ alkyl); and $R^4$ is $C_1$-$C_6$ alkyl.

In one embodiment, the disclosure provides compounds as described above with any reference to formulae (I)-(III), wherein $R^1$ is $C_6$-$C_{20}$ alkyl; $C_6$-$C_{20}$ alkenyl, or $C_6$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, —$CON(R^5)_2$, cycloalkyl, aryl, heteroaryl, and heterocycle, wherein each cycloalkyl, aryl, heteroaryl, and heterocycle are optionally substituted with $R^9$;
  where each $R^5$ independently is hydrogen, $C_1$-$C_6$ alkyl, or halo($C_1$-$C_6$ alkyl);
  wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$; where each $R^6$ independently is hydrogen or $C_1$-$C_6$ alkyl;

$R^3$ is $C_1$-$C_6$ alkyl or —$OR^7$, where $R^7$ is hydrogen, $C_1$-$C_6$ alkyl, halo($C_1$-$C_6$ alkyl), or —$CO(C_1$-$C_6$ alkyl); and $R^4$ is hydrogen, or $C_1$-$C_6$ alkyl.

In one embodiment, the disclosure provides compounds as described above with any reference to formulae (I)-(III), wherein $R^1$ is $C_6$-$C_{20}$ alkyl, $C_6$-$C_{20}$ alkenyl, or $C_6$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, and —$CON(R^5)_2$; where each $R^5$ independently is hydrogen, $C_1$-$C_6$ alkyl, or halo($C_1$-$C_6$ alkyl);

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$; where each $R^6$ independently is hydrogen or $C_1$-$C_6$ alkyl;

$R^3$ is $C_1$-$C_6$ alkyl or —$OR^7$, where $R^7$ is hydrogen, $C_1$-$C_6$ alkyl, halo($C_1$-$C_6$ alkyl), or —$CO(C_1$-$C_6$ alkyl); and $R^4$ is hydrogen, or $C_1$-$C_6$ alkyl.

In one embodiment, the disclosure provides compounds as described above with any reference to formulae (I)-(III), wherein $R^1$ is $C_6$-$C_{20}$ alkyl, $C_6$-$C_{20}$ alkenyl, or $C_6$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, and —$CON(R^5)_2$; where each $R^5$ independently is hydrogen, $C_1$-$C_6$ alkyl, or halo($C_1$-$C_6$ alkyl);

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$; where each $R^6$ independently is hydrogen or $C_1$-$C_6$ alkyl;

$R^3$ is —$OR^7$, where $R^7$ is hydrogen, $C_1$-$C_6$ alkyl, halo($C_1$-$C_6$ alkyl), or —$CO(C_1$-$C_6$ alkyl); and $R^4$ is hydrogen, or $C_1$-$C_6$ alkyl.

In another embodiment, the disclosure provides compounds as described above with any reference to formulae (I)-(III), wherein $R^1$ is $C_6$-$C_{20}$ alkyl, $C_6$-$C_{20}$ alkenyl, or $C_6$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, and —$CON(R^5)_2$; where each $R^5$ independently is hydrogen, $C_1$-$C_6$ alkyl, or halo($C_1$-$C_6$ alkyl);

$R^2$ is $C_1$-$C_4$ alkyl, $C_2$-$C_4$ alkenyl, or $C_2$-$C_4$ alkynyl, each optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$; where each $R^6$ independently is hydrogen or $C_1$-$C_6$ alkyl;

$R^3$ is —$OR^7$, where $R^7$ is hydrogen, $C_1$-$C_6$ alkyl; halo($C_1$-$C_6$ alkyl), or —$CO(C_1$-$C_6$ alkyl); and $R^4$ is $C_1$-$C_6$ alkyl.

In one embodiment, the disclosure provides compounds as described above with any reference to formulae (I)-(III), wherein $R^1$ is $C_7$-$C_{20}$ alkyl, $C_7$-$C_{20}$ alkenyl, or $C_7$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, —$CON(R^5)_2$, cycloalkyl, aryl, heteroaryl, and heterocycle, wherein each cycloalkyl, aryl, heteroaryl, and heterocycle are optionally substituted with $R^9$;
  where each $R^5$ independently is hydrogen, $C_1$-$C_6$ alkyl, or halo($C_1$-$C_6$ alkyl);
  wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$; where each $R^6$ independently is hydrogen or $C_1$-$C_6$ alkyl;

$R^3$ is $C_1$-$C_6$ alkyl or —$OR^7$, where $R^7$ is hydrogen, $C_1$-$C_6$ alkyl, halo($C_1$-$C_6$ alkyl), or —$CO(C_1$-$C_6$ alkyl); and $R^4$ is hydrogen, or $C_1$-$C_6$ alkyl.

In one embodiment, the disclosure provides compounds as described above with any reference to formulae (I)-(III), wherein $R^1$ is $C_7$-$C_{20}$ alkyl, $C_7$-$C_{20}$ alkenyl, or $C_7$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, —$CON(R^5)_2$, cycloalkyl, aryl, heteroaryl, and heterocycle, wherein each cycloalkyl, aryl, heteroaryl, and heterocycle are optionally substituted with $R^9$;
  where each $R^5$ independently is hydrogen, $C_1$-$C_6$ alkyl, or halo($C_1$-$C_6$ alkyl);
  wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$; where each $R^6$ independently is hydrogen or $C_1$-$C_6$ alkyl;

$R^3$ is —$OR^7$, where $R^7$ is hydrogen, $C_1$-$C_6$ alkyl, halo($C_1$-$C_6$ alkyl), or —$CO(C_1$-$C_6$ alkyl); and $R^4$ is hydrogen, or $C_1$-$C_6$ alkyl.

In one embodiment, the disclosure provides compounds as described above with any reference to formulae (I)-(III), wherein $R^1$ is $C_7$-$C_{20}$ alkyl, $C_7$-$C_{20}$ alkenyl, or $C_7$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5{}_2$, —$CO_2R^5$, and —$CON(R^5)_2$; where each $R^5$ independently is hydrogen, $C_1$-$C_6$ alkyl, or halo($C_1$-$C_6$ alkyl);

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6{}_2$, —$CO_2R^6$, and —$CONR^6{}_2$; where each $R^6$ independently is hydrogen or $C_1$-$C_6$ alkyl;

$R^3$ is —$OR^7$, where $R^7$ is hydrogen, $C_1$-$C_6$ alkyl, halo($C_1$-$C_6$ alkyl), or —$CO(C_1$-$C_6$ alkyl); and $R^4$ is hydrogen, or $C_1$-$C_6$ alkyl.

In one embodiment, the disclosure provides compounds as described above with any reference to formulae (I)-(III), wherein $R^1$ is $C_7$-$C_{20}$ alkyl, $C_7$-$C_{20}$ alkenyl, or $C_7$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5{}_2$, —$CO_2R^5$, —$CON(R^5)_2$, cycloalkyl, aryl, heteroaryl, and heterocycle,
wherein each cycloalkyl, aryl, heteroaryl, and heterocycle are optionally substituted with $R^9$;
where each $R^5$ independently is hydrogen, $C_1$-$C_6$ alkyl, or halo($C_1$-$C_6$ alkyl);
wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6{}_2$, —$CO_2R^6$, and —$CONR^6{}_2$; where each $R^6$ independently is hydrogen or $C_1$-$C_6$ alkyl;

$R^3$ is —$OR^7$, where $R^7$ is hydrogen, $C_1$-$C_6$ alkyl, halo($C_1$-$C_6$ alkyl), or —$CO(C_1$-$C_6$ alkyl); and $R^4$ is $C_1$-$C_6$ alkyl.

In another embodiment, the disclosure provides compounds as described above with any reference to formulae (I)-(III), wherein $R^1$ is $C_7$-$C_{20}$ alkyl, $C_7$-$C_{20}$ alkenyl, or $C_7$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5{}_2$, —$CO_2R^5$, and —$CON(R^5)_2$; where each $R^5$ independently is hydrogen, $C_1$-$C_6$ alkyl, or halo($C_1$-$C_6$ alkyl);

$R^2$ is $C_1$-$C_4$ alkyl, $C_2$-$C_4$ alkenyl, or $C_2$-$C_4$ alkynyl, each optionally substituted with one to four substituents selected from halogen, cyano, nitro, $C_1$-$C_6$ alkyl, halo($C_1$-$C_6$ alkyl), —$OR^6$, —$NR^6{}_2$, —$CO_2R^6$, and —$CONR^6{}_2$; where each $R^6$ independently is hydrogen or $C_1$-$C_6$ alkyl;

$R^3$ is —$OR^7$, where $R^7$ is hydrogen, $C_1$-$C_6$ alkyl, halo($C_1$-$C_6$ alkyl), or —$CO(C_1$-$C_6$ alkyl); and $R^4$ is $C_1$-$C_6$ alkyl.

In one embodiment, the disclosure provides compounds as described above with any reference to formulae (I)-(III), wherein $R^1$ is $C_7$-$C_{20}$ alkyl, $C_7$-$C_{20}$ alkenyl, or $C_7$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5{}_2$, —$CO_2R^5$, —$CON(R^5)_2$, cycloalkyl, aryl, heteroaryl, and heterocycle,
wherein each cycloalkyl, aryl, heteroaryl, and heterocycle are optionally substituted with $R^9$;
where each $R^5$ independently is hydrogen, $C_1$-$C_6$ alkyl, or halo($C_1$-$C_6$ alkyl);
wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6{}_2$, —$CO_2R^6$, and —$CONR^6{}_2$; where each $R^6$ independently is hydrogen or $C_1$-$C_6$ alkyl;

$R^3$ is hydrogen, halogen, $C_1$-$C_6$ alkyl, $C_2$-$C_6$ alkenyl, $C_2$-$C_6$ alkynyl, or —$OR^7$, where $R^7$ is hydrogen, $C_1$-$C_6$ alkyl, halo($C_1$-$C_6$ alkyl), or —$CO(C_1$-$C_6$ alkyl); and $R^4$ is hydrogen; $C_1$-$C_6$ alkyl, $C_2$-$C_6$ alkenyl, $C_2$-$C_6$ alkynyl, $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^7$,
wherein each $R^8$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In another embodiment, the disclosure provides compounds as described above with any reference to formulae (I)-(III), wherein $R^1$ is $C_7$-$C_{20}$ alkyl, $C_7$-$C_{20}$ alkenyl, or $C_7$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5{}_2$, —$CO_2R^5$, and —$CON(R^5)_2$;
where each $R^5$ independently is hydrogen, $C_1$-$C_6$ alkyl, Or halo($C_1$-$C_6$ alkyl);

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6{}_2$, —$CO_2R^6$, and —$CONR^6{}_2$; where each $R^6$ independently is hydrogen or $C_1$-$C_6$ alkyl;

$R^3$ is hydrogen, halogen, $C_1$-$C_6$ alkyl, $C_2$-$C_6$ alkenyl, $C_2$-$C_6$ alkynyl, or —$OR^7$, where $R^7$ is hydrogen, $C_1$-$C_6$ alkyl, halo($C_1$-$C_6$ alkyl), or —$CO(C_1$-$C_6$ alkyl); and $R^4$ is hydrogen, $C_1$-$C_6$ alkyl, $C_2$-$C_6$ alkenyl, $C_2$-$C_6$ alkynyl, $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^7$,
wherein each $R^8$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In yet another embodiment, the disclosure provides compounds as described above with any reference to formulae (I)-(III), wherein $R^1$ is $C_7$-$C_{20}$ alkyl, $C_7$-$C_{20}$ alkenyl, or $C_7$-$C_{20}$ alkynyl, each optionally substituted with one to four substituents selected from halogen, cyano, nitro; $C_1$-$C_6$ alkyl, halo($C_1$-$C_6$ alkyl), —$OR^5$, —$NR^5{}_2$, —$CO_2R^5$, and —$CON(R^5)_2$;
where each $R^5$ independently is hydrogen, $C_1$-$C_6$ alkyl, or halo($C_1$-$C_6$ alkyl);

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6{}_2$, —$CO_2R^6$, and —$CONR^6{}_2$; where each $R^6$ independently is hydrogen or $C_1$-$C_6$ alkyl;

$R^3$ is $C_1$-$C_6$ alkyl, $C_2$-$C_6$ alkenyl, $C_2$-$C_6$ alkynyl, or —$OR^7$, where $R^7$ is hydrogen, $C_1$-$C_6$ alkyl, halo($C_1$-$C_6$ alkyl), or —CO($C_1$-$C_6$ alkyl); and $R^4$ is hydrogen, $C_1$-$C_6$ alkyl, $C_2$-$C_6$ alkenyl, $C_2$-$C_6$ alkynyl, $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^7$, wherein each $R^8$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In yet another embodiment, the disclosure provides compounds as described above with any reference to formulae (I)-(III), wherein $R^1$ is $C_7$-$C_{20}$ alkyl, $C_7$-$C_{20}$ alkenyl, or $C_7$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, —$CON(R^5)_2$, cycloalkyl, aryl, heteroaryl, and heterocycle, wherein each cycloalkyl, aryl, heteroaryl, and heterocycle are optionally substituted with $R^9$;

where each $R^5$ independently is hydrogen, $C_1$-$C_6$ alkyl, or halo($C_1$-$C_6$ alkyl);

wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$; where each $R^6$ independently is hydrogen or $C_1$-$C_6$ alkyl;

$R^3$ is $C_1$-$C_6$ alkyl or —$OR^7$, where $R^7$ is hydrogen, $C_1$-$C_6$ alkyl, halo($C_1$-$C_6$ alkyl), or —CO($C_1$-$C_6$ alkyl); and $R^4$ is hydrogen, $C_1$-$C_6$ alkyl, $C_2$-$C_6$ alkenyl, $C_2$-$C_6$ alkynyl, $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^7$, wherein each $R^8$ independently is halogen, cyano, intro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In yet another embodiment, the disclosure provides compounds as described above with any reference to formulae (I)-(III), wherein $R^1$ is $C_7$-$C_{20}$ alkyl, $C_7$-$C_{20}$ alkenyl, or $C_7$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, and —$CON(R^5)_2$; where each $R^5$ independently is hydrogen, $C_1$-$C_6$ alkyl, or halo($C_1$-$C_6$ alkyl);

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$; where each $R^6$ independently is hydrogen or $C_1$-$C_6$ alkyl;

$R^3$ is $C_1$-$C_6$ alkyl or —$OR^7$, where $R^7$ is hydrogen, $C_1$-$C_6$ alkyl, halo($C_1$-$C_6$ alkyl), or —CO($C_1$-$C_6$ alkyl); and $R^4$ is hydrogen, $C_1$-$C_6$ alkyl, $C_2$-$C_6$ alkenyl, $C_2$-$C_6$ alkynyl, $C_3$-$C_8$cycloalkyl($C_1$-$C_6$ alkyl), aryl($C_1$-$C_6$ hetero aryl($C_1$-$C_6$ alkyl), or hetero cycle($C_1$-$C_6$ alkyl), wherein each cycloalkyl, aryl, heteroaryl, and heterocycle are optionally substituted with $R^7$, wherein each $R^8$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In yet another embodiment, the disclosure provides compounds as described above with any reference to formulae (I)-(III), wherein $R^1$ is $C_7$-$C_{20}$ alkyl, $C_7$-$C_{20}$ alkenyl, or $C_7$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$NR^5_2$, —$CO_2R^5$, —$CON(R^5)_2$, cycloalkyl, aryl, heteroaryl, and heterocycle, wherein each cycloalkyl, aryl, heteroaryl, and heterocycle are optionally substituted with $R^9$;

where each $R^5$ independently is hydrogen, $C_1$-$C_6$ alkyl, or halo($C_1$-$C_6$ alkyl);

wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$; where each $R^6$ independently is hydrogen or $C_1$-$C_6$ alkyl;

$R^3$ is —$OR^7$, where $R^7$ is hydrogen, $C_1$-$C_6$ alkyl, halo($C_1$-$C_6$ alkyl), or —CO($C_1$-$C_6$ alkyl); and $R^4$ is hydrogen, $C_1$-$C_6$ alkyl, $C_2$-$C_6$ alkenyl, $C_2$-$C_6$ alkynyl, $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^7$, wherein each $R^8$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In yet another embodiment, the disclosure provides compounds as described above with any reference to formulae (I)-(III), wherein $R^1$ is $C_7$-$C_{20}$ alkyl, $C_7$-$C_{20}$ alkenyl, or $C_7$-$C_{20}$ alkynyl, each optionally substituted with one to four substituents selected from halogen, cyano, nitro, $C_1$-$C_6$ alkyl, halo($C_1$-$C_6$ alkyl), —$OR^5$, —$CO_2R^5$, and —$CON(R^5)_2$; where each $R^5$ independently is hydrogen, $C_1$-$C_6$ alkyl, or halo ($C_1$-$C_6$ alkyl);

$R^2$ is $C_1$-$C_4$ alkyl, $C_2$-$C_4$ alkenyl, $C_2$-$C_4$ alkynyl, or $C_1$-$C_4$ alkoxy, each optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$; where each $R^6$ independently is hydrogen or $C_1$-$C_6$ alkyl;

$R^3$ is —$OR^7$, where $R^7$ is hydrogen, $C_1$-$C_6$ alkyl, halo($C_1$-$C_6$ alkyl), or —CO($C_1$-$C_6$ alkyl); and $R^4$ is hydrogen, $C_1$-$C_6$ alkyl, $C_2$-$C_6$ alkenyl, $C_2$-$C_6$ alkynyl, $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^7$, wherein each $R^8$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino.

In another embodiment, the disclosure provides pharmaceutically acceptable salts of compounds of the disclosure. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, monofluoroacetic acid, difluoroacetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. For example, in one embodiment, the salt is a trifluoroacetic acid salt, p-toluenesulfonic acid salt, or hydrochloride salt.

Pharmaceutically acceptable salts also include salts formed when an acidic proton present in the parent compound is either replaced by an inorganic ion (e.g., an alkali metal ion such as $Na^+$, $K^+$ or $Li^+$, an alkaline earth ion such as $Ca^{2+}$ or $Mg^{2+}$, an aluminum ion, or an ammonium ion) or coordinates with an organic base (e.g., ethanolamine, diethanolamine, triethanolamine, N-methylglucamine, morpholine, piperidine, dimethylamine, diethylamine, etc.).

The compounds described herein, as well as the salts thereof, may also be in the form of hydrates, solvates and N-oxides, as are well-known in the art.

Therapeutic Applications

Compounds of the disclosure are useful, for example, for treating or suppressing diseases associated with decreased mitochondrial function resulting in diminished ATP production and/or oxidative stress and/or lipid peroxidation in a subject in need of treatment. The present disclosure provides methods of treating conditions including but not limited to Friedreich's ataxia, Leber's Hereditary Optic Neuropathy, Kearns-Sayre Syndrome, Mitochondrial Encephalomyopathy with Lactic Acidosis and Stroke-Like Episodes, and Leigh syndrome in a subject by administering an effective amount of a compound as described above with respect to any of formulae (I)-(III), including a salt or solvate or stereoisomer thereof.

The disclosure also provides methods of treating conditions including but not limited to obesity, atherosclerosis, Parkinson's Disease, cancer, heart failure, myocardial infarction (MI), Alzheimer's Disease, Huntington's Disease, schizophrenia, bipolar disorder, fragile X syndrome, chronic fatigue syndrome, and Leigh syndrome, in a subject by administering an effective amount of a compound as described above with respect to any of formulae (I)-(III), including a salt or solvate or stereoisomer thereof.

Friedreich's Ataxia

Friedreich's ataxia is a severe neurodegenerative and cardiodegenerative condition. It is characterized by progressive ataxia of the limbs, muscle weakness, dysarthria, skeletal deformities and cardiomyopathy. While the biochemical basis of the disease is still under investigation, it is strongly associated with insufficient frataxin (Wilson et al. (1997) Nat. Genet. 16, 352-357; Wilson et al. (2003) J. Neurol. Sci. 207, 103-105). In the majority of patients the insufficiency of frataxin is a consequence of an intronic GAA triplet repeat expansion in the gene for frataxin, which results in a significant decrease in its mRNA levels, and ultimately in protein levels as well (Campuzano et al. (1996) Science 271, 1423-1427; Campuzano et al. (1997) Hum. Mol. Genet. 6, 1771-1780). Frataxin acts as an iron chaperone during heme biosynthesis (Bencze et al. (2007) J.C.S. Chem. Commun. 1798-1800) and has been shown to be capable of stimulating the in vitro assembly of heme and Fe—S clusters (Park et al. (2003) J. Biol. Chem. 278, 31340-31351; Yoon et al. (2003) J. Am Chem. Soc. 125, 6078-6084; Yoon et al. (2004) J. Biol. Chem. 279, 25943-25946). Frataxin can interact physically with mitochondrial electron transport chain proteins, as well as with mitochondrial aconitase (which contains an Fe—S cluster) (Bulteau et al. (2004) Science 305, 242-245; Gonzalez-Cabo et al. (2005) Hum. Mol. Genet. 14, 2091-2098). Therefore, frataxin deficiency results in disruption of cellular iron homeostasis, with a progressive iron accumulation in the mitochondrion, and a deficiency in heme and Fe—S clusters.

It is believed that a deficiency in frataxin leads to compromised mitochondrial respiratory chain function through a failure to assemble one or more Fe-utilizing proteins; one or more Fe—S clusters in the mitochondrial respiratory complexes are likely to represent a critical locus. In fact, diminished function of these complexes has been noted in Friedreich's ataxia patients (Bradley et al. (2000) Hum. Mol. Genet. 9, 275-282). The loss of mitochondrial respiratory chain function can lead to diminished ATP production, while the accumulation of Fe in the mitochondria makes the organelle highly susceptible to oxidative damage by reactive oxygen species, whose concentration increases concomitant with the decrease in respiratory chain function. There is compelling evidence that while oxidative damage is not the primary lesion in Friedreich's ataxia, oxidative stress helps to drive disease progression. Therefore, strategies to overcome oxidative stress should blunt disease progression and provide effective therapy.

Other Exemplary Mitochondrial Diseases

Leber hereditary optic neuropathy is associated with degeneration of retinal ganglion cells and causes progressive loss of vision resulting in various degrees of blindness. Leber hereditary optic neuropathy primarily affects men over the age of 20 and is maternally transmitted due to mutations in the mitochondrial (not nuclear) genome.

Kearns-Sayre syndrome is a rare neuromuscular disorder typically with onset usually before the age of 20. It is characterized by progressive external ophthalmoplegia (paralysis of the eye muscles) and mild skeletal muscle weakness, hearing loss, loss of coordination, heart problems, and cognitive delays. There are many other names for the Kearns-Sayre syndrome including: Chronic progressive external ophthalmoplegia CPEO with myopathy; CPEO with ragged-red fibers; KSS; Mitochondrial cytopathy, Kearns-Sayre type; Oculocraniosomatic syndrome; Ophthalmoplegia-plus syndrome; Ophthalmoplegia with myopathy; and Ophthalmoplegia with ragged-red fibers.

Mitochondrial Encephalomyopathy with Lactic Acidosis and Stroke-Like Episodes is a progressive mitochondrial disease that involves multiple organ systems including the central nervous system, cardiac muscle, skeletal muscle, and gastrointestinal system. Symptoms include muscle weakness, stroke-like events, eye muscle paralysis, and cognitive impairment. Leigh syndrome is a degenerative brain disorder is usually diagnosed at a young age (e.g. before age two). Deterioration is often rapid with symptoms such as seizures, dementia, feeding and speech difficulties, respiratory dysfunction, heart problems, and muscle weakness. Prognosis is poor with death typically occurring within a few years of diagnosis.

Mitochondrial Energy Production

Energy released from the citric acid (Krebs) cycle in the mitochondrial matrix enters the mitochondrial electron transport chain as NADH (complex I) and $FADH_2$ (complex II). These are the first two of five protein complexes involved in ATP production, all of which are located in the inner mitochondrial membrane. Electrons derived from NADH (by oxidation with a NADH-specific dehydrogenase) and $FADH_2$ (by oxidation with succinate dehydrogenase) travel down the respiratory chain, releasing their energy in discrete steps by driving the active transport of protons from the mitochondrial matrix to the intermembrane space (i.e., through the inner mitochondrial membrane). The electron carriers in the respiratory chain include flavins, protein-bound iron-sulfur centers, quinones, cytochromes and copper. There are to molecules that transfer electrons between complexes: coenzyme Q (complex I→III, and complex II→III) and cytochrome c (complex III→IV). The final electron acceptor in the respiratory chain is $O_2$, which is converted to $H_2O$ in complex IV.

In a functional mitochondrion, transport of two electrons through complex I results in the transport of $4H^+$ into the intermembrane space. Two more $H^+$ transfers to the intermembrane space result from electron transport through complex III, and four more $H^+$ transfers from electron transport through complex IV. The 10 electrons transported to the intermembrane space create a proton electrochemical gradient; they can return to the mitochondrial matrix via complex V (ATP synthase), with the concomitant conversion of ADP to ATP. It is interesting that no $H^+$ is transferred to the intermembrane space as a consequence of electron transport through complex II. Therefore, $2e^-$ transfer from $FADH_2$ (complex II→complex III→complex IV) results in the transport of only 6 protons, compared with 10 protons resulting from $2e^-$ transfer from NADH (complex I→complex III→complex IV), with correspondingly less ATP produced. Each glucose molecule metabolized by glycolysis produces 12 electrons; these are converted to 5 NADH molecules and 1 $FADH_2$ via the Krebs cycle in the mitochondrial matrix. The 5 NADH molecules employed in mitochondrial electron transport produce about 25 ATPs, while the single $FADH_2$ affords only about 3 ATP molecules. (There are another 4 molecules of ATP derived from glucose metabolism—2 during glycolysis and 2 in the Krebs cycle). While this analysis underscores the importance of complex I involvement in normal ATP production, it also tends to obscure certain metabolic realities/uncertainties that may offer important opportunities for therapeutic intervention. One metabolic reality is that complex I, while important quantitatively for ATP production in normal mitochondria, is not essential for all mitochondrial ATP production. Electrons can enter the electron transport chain at the level of coenzyme Q (either from complex II or from fatty acid oxidation), producing about 60% as much ATP as would have resulted had they entered the electron transport chain at complex I). While the flux of electrons that normally enter the individual mitochondrial complexes, ultimately passing through coenzyme Q, is probably dictated largely by the availability of electrons derived from NADH, $FADH_2$ and fatty acid oxidation, the actual intrinsic capacity of the individual pathways does not appear to have been studied carefully.

In functional mitochondria, a few experimental parameters can be measured readily, reflecting mitochondrial respiration. These include NADH and $O_2$ consumption, and ATP production. Less readily measured are the electrons that flow through the electron transport chain, thereby consuming oxygen, and producing $H_2O$ and ATP. The electrons within the mitochondria can really only be measured when they are associated with one of the mitochondrial electron carriers such as coenzyme Q. In humans, this mitochondrial coenzyme is present as coenzyme $Q_{10}$, which has a 50-carbon C-substituent that renders the molecule virtually insoluble in water (calculated octanol-water partition coefficient>$10^{20}$) (James et al. (2005) *J Biol. Chem.* 280, 21295-21312).

In dysfunctional mitochondria, one can still carry out the same types of measurements as noted above for functioning mitochondria. If the flow of electrons through complex I is interrupted, several measured parameters should change. These include diminished consumption of NADH (measured as increased lactate through pyruvate reduction) and diminished ATP production. Since electrons will not flow as efficiently from complex I to coenzyme Q, the concentration of this reduced coenzyme will diminish. Interestingly, a new pathway for oxygen consumption is created. While oxygen is not converted as efficiently to water in complex IV (an overall four electron reduction of each oxygen molecule), much of the flow of electrons into a defective complex I is redirected to oxygen, with the production of superoxide (a one electron reduction of each oxygen). Thus, the stoichiometry of oxygen utilization is altered. The production of superoxide by mitochondria actually occurs to some extent even in normal mitochondria, but is a much more frequent event in mitochondria containing defects in the respiratory chain. Superoxide is one form of reactive oxygen species (ROS). Superoxide itself is not believed to react readily with biological molecules such lipid membranes, proteins and DNA, and actually functions as a signaling molecule for the regulation of certain cellular processes. Biologically, the main fate of superoxide ($O^-._2$) is a disproportionation reaction with itself to produce peroxide ($H_2O_2$) and oxygen, i.e.

$$2O^-._2 + 2H^+ \rightarrow H_2O_2 + O_2$$

This reaction occurs spontaneously, and can also be catalyzed by superoxide dismutase. Superoxide can also be reduced to peroxide in a monovalent process. Like superoxide, hydrogen peroxide is also not intrinsically deleterious to cellular macromolecules, and is actually essential to the function of a number of enzymes. However, in the presence of metal ions such as iron and copper, hydrogen peroxide is converted to hydroxyl radical (HO.) and hydroxide ion ($OH^-$) according to the Fenton reaction, i.e.

$$HOOH + Fe^{2+} \rightarrow Fe^{3+} + HO. + OH^-$$

Hydroxyl radicals are very highly reactive, capable of reacting with virtually any biological molecule, including DNA, proteins and lipids. Hydroxyl radicals can also diffuse through cells readily, and their ability to damage cells is limited only by the distance that they travel before they react. Hydroxyl radicals can also react with superoxide, producing singlet oxygen (($^1O_2$)+OH_), another highly reactive form of ROS that damages cellular macromolecules and assemblies. One particularly deleterious and well-studied reaction mediated by hydroxyl radicals is the abstraction of hydrogen atoms (H.) from membrane lipids, forming a carbon-centered radical (R.). This radical $$HO. + RH(lipid) \rightarrow R. + H_2O$$

$$R. + O_2 \rightarrow ROO.$$

$$ROO. + RH \rightarrow ROOH + R.$$

can readily react with oxygen, forming a hydroperoxy radical (ROO.). The hydroperoxy radical is also highly reactive, and can abstract another hydrogen atom from the membrane lipid, producing another carbon-centered radical (which can undergo precisely the same chemistry), ultimately producing a chain reaction affording many oxidative lesions in the membrane lipids from a single hydroxyl radical (lipid peroxidation). It is for this reason that lipid peroxidation likely represents a major process by which cellular and mitochondrial membranes are degraded in cells containing (partially) dysfunctional mitochondria. The observed accumulation of lipofuscin in Friedreich's ataxia patients is fully consistent with the thesis that lipid peroxidation is a central process that drives disease progression (La Marche et al. (1980) *Can. J. Neurosci.* 7, 389-396; Yin, D. (1996) *Free Rad. Biol. Med.* 21, 871-888; Yamada et al. (2001) *J. Lipid Res.* 42, 1187-1196).

It may be noted that while all lesions in the mitochondrial electron transport chain that affect mitochondrial dysfunction will result in elevated levels of superoxide, some types of lesions may be expected to produce more functional damage. The latter would certainly include Friedreich's ataxia, in which suboptimal levels of the protein frataxin (which is responsible for cellular iron homeostasis; Park et al. (2003) *J. Biol. Chem.* 278, 31340-31351; Yoon et al. (2003) *J. Am. Chem. Soc.* 125, 6078-6084; Yoon et al. (2004) *J. Biol. Chem.* 279, 25943-25946; Bencze et al. (2007) *J.C.S. Chem. Commun.* 1798-1800) results in an accumulation of $Fe^{2+/3+}$ within the mitochondria, and contributes instead to the Fenton chemistry noted above. Likewise, disorders such as amyotrophic lateral sclerosis are associated with a deficiency in the detoxifying enzyme superoxide dismutase, and will have greatly enhanced concentrations of the ROS discussed above.

One poorly studied parameter of mitochondrial electron transport is whether the process is best characterized as involving one or two electron transfers. The is important because NADH is an obligatory two-electron donor, and coenzyme Q and cytochrome c participate in two-electron redox cycles, as does $FADH_2$. Virtually all publications represent the processes in which these species participate as involving a net two electron change. However, $FADH_2$ may (and generally does) transfer its reducing equivalents as single electrons. Further, the Q cycle in complex III clearly involves single-electron transfers. Reduced cytochrome c is known to transfer electrons one at a time to cytochrome c oxidase, the enzyme responsible for the final step in respiration. Finally, the accumulation of electrons within dysfunctional mitochondria (producing reductive stress) is relieved substantially by (one-electron) reduction of oxygen to superoxide (vide supra). Thus, while the electron transport chain has the capacity to transfer two electrons by virtue of the redox cycles of most of its participants, it is not clear that it necessarily must do so to function.

Given that the reductive stress (build-up of electrons) encountered initially in mitochondrial dysfunction is a one electron process, as is lipid peroxidation, carriers of single electrons could find utility in dealing with reductive stress, e.g. molecules in which the one-electron reduced intermediate is stabilized by dipole interactions, substituent effects, resonance effects or captodative effects. Molecules designed to traffic single electrons, and which can (i) accept electrons from superoxide (ii) donate electrons to complex III and (iii) quench carbon-centered lipid radicals are especially useful. Multifunctional Radical Quenchers (MRQs) of the invention can effectively protect mitochondria, cells and organisms from oxidative stress.

Pharmaceutical Compositions

In another aspect, the present disclosure provides compositions comprising one or more of compounds as described above with respect to any of formulae (I)-(III) and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgGisotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound(s) may be manufactured by means of conventional mixing, dissolving; granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection; as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known.

For buccal administration, the compositions may take the form of tablets or lozenges formulated in conventional manner.

For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, diohlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active metabolite compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect.

For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective local dosages without undue experimentation.

DEFINITIONS

The following terms and expressions used herein have the indicated meanings.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3 (4H)-on-5-yl, 2H-benzo[b][1,4]oxazin3 (4H)-on-6-yl, 2H-benzo[b][1,4]oxazin3 (4H)-on-7-yl, 2H-benzo[b][1,4]oxazin3 (4H)-on-8-yl, benzo[d]oxazin-2(3H)-on-5-yl, benzo[d]oxazin-2 (3H)-on-6-yl, benzo[d]oxazin-2(3H)-on-7-yl, benzo[d]oxazin-2 (3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydro quinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydro quinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, tlniazolidinyl, thiomorpholinyl, 1,1-dioxidothiomorpholinyl (thiomorpholinesulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "nitro" as used herein, means a —NO$_2$ group.

The term "saturated" as used herein means the referenced chemical structure does not contain any multiple carbon-carbon bonds. For example, a saturated cycloalkyl group as defined herein includes cyclohexyl, cyclopropyl, and the like.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

"Pharmaceutically acceptable" refers to those compounds, materials, compositions, and/or dosage forms which are; within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Modulating" or "modulate" refers to the treating, prevention, suppression, enhancement or induction of a function, condition or disorder. For example, it is believed that the compounds of the present invention can modulate atherosclerosis by stimulating the removal of cholesterol from atherosclerotic lesions in a human.

"Treating" or "treatment" as used herein covers the treatment of a disease or disorder described herein, in a subject, preferably a human, and includes:

i. inhibiting a disease or disorder, i.e., arresting its development;

ii. relieving a disease or disorder, i.e., causing regression of the disorder;

iii. slowing progression of the disorder; and/or, iv. inhibiting, relieving, or slowing progression of one or more symptoms of the disease or disorder.

"Subject" refers to a warm blooded animal such as a mammal, preferably a human, or a human child, which is afflicted with, or has the potential to be afflicted with one or more diseases and disorders described herein.

"$EC_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

Methods of Synthesis

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern. Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. O. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg ThiemeVerlag, Stuttgart 1974, in H.-D. Jakubke and H. Jescheit, "Aminosauren, Peptide, Protein", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

EXAMPLES

The compounds and methods of the disclosure are illustrated further by the following examples, which are provided for illustrative purposes and are not intended to be construed as limiting the disclosure in scope or spirit to the specific compounds and methods described in them.

Chemicals and solvents were of reagent grade and were used without further purification. All reactions involving air or moisture-sensitive reagents or intermediates were performed under an argon atmosphere. Flash chromatography was carried out using Silicycle 200-400 mesh silica gel. Analytical TLC Was carried out using 0.25 mm EM silica gel 60 $F_{250}$ plates that were visualized by irradiation (254 nm) or by staining with p-anisaldehyde stain. HPLC separations were performed on a Waters 600 series HPLC multi-solvent delivery system using a Kratos 747 UV detector. $^1$H NMR and $^{13}$C NMR spectra were obtained using Inova 400 or 500 MHz Varian instruments. Chemical shifts were reported in parts per million (ppm, δ) referenced to the residual $^1$H resonance of the solvent ($CDCl_3$, 7.26 ppm). $^{13}$C spectra were referenced to the residual $^{13}$C resonance of the solvent ($CDCl_3$, 77.0 ppm). Splitting patterns were designated as follows: s, singlet; br, broad; d, doublet; dd; doublet of doublets; t, triplet; q, quartet; m, multiplet. High resolution mass spectra were obtained in the Arizona State University CLAS High Resolution Mass Spectrometry Laboratory.

Example 1

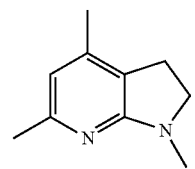

1,4,6-Trimethyl-2,3-dihydro-1H-pyrrolo[2,3-b]pyridine

To a solution of 2.36 g (23.8 mmol) of (Z)-4-aminopent-3-en-2-one in 8 mL of toluene was added 5.88 g (40.5 mmol) of 2,2-dimethoxy-1-methylpyrrolidine. The reaction mixture was heated at reflux and stirred for 2 h, cooled to 90° C., and then treated with 4.65 g (48.4 mmol) of t-BuONa and 4 mL of t-BuOH. The reaction mixture was stirred at 90° C. for another 16 h. The cooled reaction mixture was quenched by the addition of 20 mL of sat aq NH₄Cl. The mixture was extracted with EtOAc. The combined organic layer was washed with brine, dried (MgSO₄) and concentrated under diminished pressure. The residue was purified by flash chromatography on a silica gel column (25 2.6 cm). Elution with 10:1 hexanes/ethyl acetate gave the product as a yellow oil: yield 1.60 g (42%); silica gel TLC R$_f$ 0.15 (4:1 hexanes/ethyl acetate); ¹H NMR (CDCl₃) δ 2.05 (s, 3H), 2.32 (s, 3H), 2.76 (t, 2H, J=8.4 Hz), 2.86 (s, 3H), 3.34 (t, 2H, J=8.4 Hz) and 6.10 (s, 1H); ¹³C NMR (CDCl₃) δ 17.8, 24.0, 24.3, 33.1, 52.4, 113.1, 118.1, 141.2, 154.5 and 163.7; mass spectrum, m/z 162.1 (M⁺) (theoretical 162.1).

Example 2

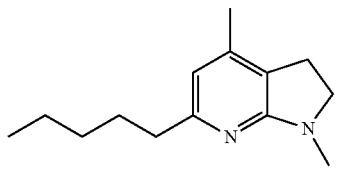 [SMILES: CCCCCc1cc(C)c2c(n1)N(C)CC2]

1,4-Dimethyl-6-pentyl-2,3-dihydro-1H-pyrrolo[2,3-b]pyridine

To a solution of 225 mg (1.39 mmol) of 1,4,6-trimethyl-2,3-dihydro-1H-pyrrolo[2,3-b]pyridine in 4 mL of THF was added 1.39 mL (2.22 mmol, 1.6 M in hexanes) of n-BuLi followed by 157 μL (1.46 mmol) of 1-bromobutane at −78° C. The reaction mixture was slowly warmed to room temperature and stirred for another 16 h. The reaction mixture was quenched by the addition of 10 mL of sat aq NH₄Cl at 0° C. The mixture was extracted with EtOAc. The combined organic layer was washed with brine, dried (MgSO₄) and concentrated under diminished pressure. The residue was purified by flash chromatography on a silica gel column (25 3.2 cm). Elution with 10:1 hexanes/ethyl acetate gave the product as a yellow oil: yield 0.20 g (66%); silica gel TLC R$_f$ 0.15 (8:1:1 hexanes/ethyl acetate/MeOH); ¹H NMR (CDCl₃) δ 0.88 (t, 3H, J=7.2 Hz), 1.30-1.36 (m, 4H), 1.66 (quint, 2H, J=7.6 Hz), 2.08 (s, 3H), 2.55 (t, 2H, J=8.0 Hz), 2.81 (t, 2H, J=8.0 Hz), 2.88 (s, 3H), 3.38 (t, 2H, J=8.0 Hz) and 6.13 (s, 1H); ¹³C NMR (CDCl₃) δ 14.1, 18.0, 22.6, 24.4, 29.6, 31.8, 33.3, 38.0, 52.5, 112.4, 118.2, 141.1, 159.1 and 163.7; mass spectrum, m/z 218.2 (M⁺) (theoretical 218.3); mass spectrum (APCI), m/z 219.1864 (M+H)⁺ (C₁₄H₂₃N₂ requires 219.1861).

Example 3

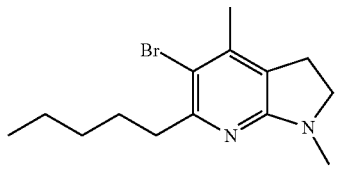 [SMILES: CCCCCc1nc2c(c(C)c1Br)CCN2C]

5-Bromo-1,4-dimethyl-6-pentyl-2,3-dihydro-1H-pyrrolo[2,3-b]pyridine

To a solution of 108 mg (0.50 mmol) of 1,4-dimethyl-6-pentyl-2,3-dihydro-1H-pyrrolo[2,3-b]pyridine in 3 mL of chloroform was added 70.7 mg (0.25 mmol) of 1,3-dibromo-5,5-dimethylhydantoin in portions at 0° C. The reaction mixture was stirred at 0° C. for 30 min. The reaction was quenched by the addition of 5 mL of sat aq. NaHCO₃. The mixture was extracted with chloroform and the combined organic layer was washed with brine and dried over MgSO₄. The concentrated residue was purified by flash chromatography on a silica gel column (20 1.7 cm). Elution with 100:1 hexanes/ethyl acetate gave the product as a yellow oil: yield 136 mg (92%); silica gel TLC R$_f$ 0.65 (8:1:1 hexanes/ethyl acetate/methanol); ¹H NMR (CDCl₃) δ 0.89 (t, 3H, J=7.2 Hz), 1.33-1.38 (m, 4H), 1.66 (quint, 2H, J=7.6 Hz), 2.16 (s, 3H), 2.77 (t, 2H, J=8.0 Hz), 2.82-2.87 (m, 5H) and 3.40 (t, 2H, J=8.0 Hz); ¹³C NMR (CDCl₃) δ 14.1, 19.5, 22.6, 25.2, 28.4, 31.8, 33.0, 38.1, 52.4, 110.9, 120.4, 141.1, 156.8 and 161.8; mass spectrum, m/z 297.1 and 299.1 (M+H)⁺ (theoretical 297.1 and 299.1); mass spectrum (APCI), m/z 297.0968 and 199.0937 (M+H)⁺ (C₁₄H₂₂N₂Br requires 297.0966 and 299.0946).

Example 4

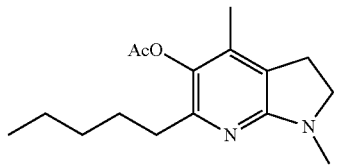 [SMILES: CCCCCc1nc2c(c(C)c1OC(C)=O)CCN2C]

1,4-Dimethyl-6-pentyl-2,3-dihydro-1H-pyrrolo[2,3-b]pyridin-5-yl acetate (2a)

To a solution of 33.0 mg (0.11 mmol) of 5-bromo-1,4-dimethyl-6-pentyl-2,3-dihydro-1H-pyrrolo[2,3-b]pyridine in 1 mL of THF was added 16.5 μL (0.11 mmol) of tetramethylethylenediamine (TMEDA) at −78° C. followed by 139 μL (0.22 mmol, 1.6 M in hexanes) of n-BuLi. After 30 min, 27.2 μL (0.24 mmol) of trimethoxy boron was added and the resulting mixture was stirred for another 1 h. To the reaction mixture was added slowly 51.4 μL (0.24 mmol, 32 wt %) of peracetic acid and the solution was then warmed to 0° C. over a period of 30 min. The mixture was diluted by 5 mL of H₂O and extracted with three 5-mL portions of EtOAc. The combined organic layer was washed with brine, dried (MgSO₄) and the solvent was concentrated under diminished pressure. The resulting oil was dissolved in 2 mL of CH₂Cl₂ at 0° C., followed by the addition of 92.8 μL (0.66 mmol) of triethylamine, 1.40 mg (0.01 mmol) of DMAP and 31.4 μL (0.33 mmol) of acetic anhydride. The reaction mixture was stirred at room temperature for 1 h and quenched by the addition of 2 mL of sat aq NH₄Cl. The solution was then extracted with three 5-mL portions of EtOAc. The combined organic layer was washed with brine, dried (MgSO₄) and the solvent was concentrated under diminished pressure. The residue was purified by flash chromatography on a silica gel column (20 1.7 cm). Elution with 100:1 hexanes/ethyl acetate gave 2a as a yellow oil: yield 26.7 mg (88%); silica gel TLC R$_f$ 0.1 (3:7 EtOAt/hexanes); ¹H NMR (CDCl₃) δ 0.90 (t, 3H, J=7.0 Hz), 1.32-1.37 (m, 4H), 1.64 (quint, 2H, J=7.5 Hz), 1.95 (s, 3H), 2.31 (s, 3H), 2.47 (t, 2H, J=8.0 Hz), 2.85 (t, 2H, J=8.0 Hz), 2.89 (s, 3H) and 3.44 (t, 2H, J=8.0 Hz); ¹³C NMR (CDCl₃) δ 14.0, 20.6, 22.5, 24.7, 28.4, 29.6, 31.8, 32.5, 33.3, 52.4, 120.1, 134.7, 136.5, 149.7, 161.2 and 169.9; mass spectrum, m/z 276.2 (M)⁺ (theoretical 276.2); mass spectrum (APCI), m/z 277.1910 (M+H)⁺ ($C_{16}H_{25}N_2O_2$ requires 277.1916).

Example 5

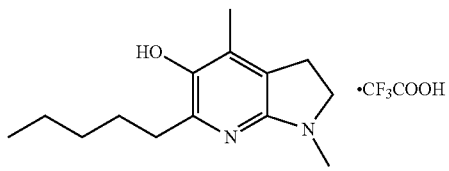 [SMILES: CCCCCc1nc2c(c(C)c1O)CCN2C ; "·CF3COOH"]

1,4-Dimethyl-6-pentyl-2,3-dihydro-1H-pyrrolo[2,3-b]pyridin-5-ol trifluoroacetic acid salt (1a)

To a solution of 20.0 mg (72.4 μmol) of 1,4-dimethyl-6-pentyl-1H-pyrrolo[2,3-b]pyridin-5-yl acetate in 1 mL of $CH_2Cl_2$ was added 217 μL (84.0 μmol, 1.0 M in hexanes) of DIBAL-H at 78° C. The reaction mixture was stirred at 78° C. for 1 h and then 2 mL of sat aq sodium potassium tartrate was added slowly. The reaction mixture was slowly warmed to room temperature over a period of 30 min. The solution was extracted with three 5-mL portions of ethyl acetate. The combined organic layer was washed with brine, dried ($MgSO_4$) and concentrated under diminished pressure to give the crude product as a yellow oil: silica gel TLC $R_f$ 0.12 (1:9 MeOH/$CH_2Cl_2$). The residue was then dissolved in 1 mL of $CH_3CN$ and 1% aq TFA, frozen and lyophilized. The crude product was purified on a Prepex $C_8$ reversed phase semi-preparative (250 mm×10 mm) HPLC column using a gradient of methanol and water. Linear gradients were employed using 1:4 methanol/water→4:1 methanol/water over a period of 20 min, and then 4:1 methanol/water→methanol over a period of 40 min, at a flow rate of 3.5 mL/min (monitoring at 260 nm). Fractions containing the desired product eluted at 21.6 min, and were collected, frozen, and lyophilized to give 1a as a light yellow solid: yield 13.5 mg (80%); ¹H NMR ($CD_3CN$) δ 0.88 (t, 3H, J=6.8 Hz), 1.27-1.32 (m, 4H), 1.54 (quint, 2H, J=7.6 Hz), 2.13 (s, 3H), 2.69 (t, 2H, J=8.0 Hz), 2.99 (t, 2H, J=8.4 Hz), 3.06 (s, 3H) and 3.72 (t, 2H, J=8.4 Hz); ¹³C NMR ($CDCl_3$) δ 13.0, 13.3, 22.1, 24.4, 27.2, 28.3, 31.1, 32.4, 53.1, 117.3, 126.1, 132.1, 140.4, 141.6 and 152.0; mass spectrum, m/z 234.2 (M)⁺ (theoretical 234.2); mass spectrum (APCI), m/z 235.1806 (M+H)⁺ ($C_{14}H_{23}N_2O$ requires 235.1810).

Example 6

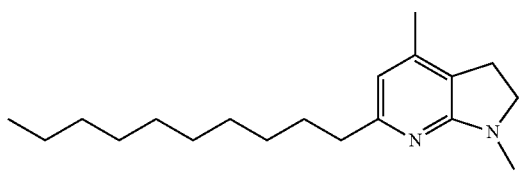 [SMILES: CCCCCCCCCCc1cc(C)c2c(n1)N(C)CC2]

1,4-Dimethyl-6-decyl-2,3-dihydro-1H-pyrrolo[2,3-b]pyridine

To a solution of 181 mg (1.12 mmol) of 1,4,6-trimethyl-2,3-dihydro-1H-pyrrolo[2,3-b]pyridine in 3 mL of THF was added 1.19 mL (1.90 mmol, 1.6 M in hexanes) of n-BuLi followed by 255 μL (1.34 mmol) of 1-bromononane at −78° C. The reaction mixture was slowly warmed to room temperature and stirred for another 16 h. The reaction mixture was quenched by the addition of 10 mL of sat aq $NH_4Cl$ at 0° C. The mixture was extracted with EtOAc. The combined organic layer was washed with brine, dried ($MgSO_4$) and concentrated under diminished pressure. The residue was purified by flash chromatography on a silica gel column (25 3.2 cm). Elution with 10:1 hexanes/ethyl acetate gave the product as a yellow oil: yield 210 mg (66%); silica gel TLC $R_f$ 0.18 (8:1:1 hexanes/ethyl acetate/MeOH); ¹H NMR ($CDCl_3$) δ 0.86 (t, 3H, J=6.8 Hz), 1.24-1.30 (m, 16H), 1.65 (quint, 2H, J=7.6 Hz), 2.08 (s, 3H), 2.54 (t, 2H, J=8.0 Hz), 2.81 (t, 2H, J=8.0 Hz), 2.90 (s, 3H), 3.38 (t, 2H, J=8.0 Hz) and 6.13 (s, 1H); ¹³C NMR ($CDCl_3$) δ 14.2, 18.1, 22.8, 24.5, 29.5, 29.68, 29.73, 29.75, 29.77, 30.1, 32.1, 33.4, 38.2, 52.6, 112.6, 118.4, 141.3, 159.3 and 163.9; mass spectrum, m/z 288.3 (M⁺) (theoretical 288.3); mass spectrum (APCI), m/z 289.2653 (M+H)⁺ ($C_{19}H_{33}N_2$ requires 289.2644).

Example 7

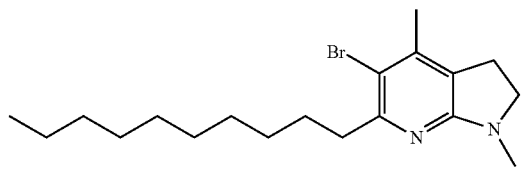 [SMILES: CCCCCCCCCCc1nc2c(c(C)c1Br)CCN2C]

5-Bromo-1,4-dimethyl-6-decyl-2,3-dihydro-1H-pyrrolo[2,3-b]pyridine

To a solution of 286 mg (0.99 mmol) of 1,4-dimethyl-6-decyl-2,3-dihydro-1H-pyrrolo[2,3-b]pyridine in 4 mL of chloroform was added 143 mg (0.50 mmol) of 1,3-dibromo-5,5-dimethylhydantoin in portions at 0° C. The reaction mixture was stirred at 0° C. for 30 min. The reaction was quenched by the addition of 5 mL of sat aq $NaHCO_3$. The mixture was extracted with chloroform and the combined organic layer was washed with brine and dried over $MgSO_4$. The concentrated residue was purified by flash chromatography on a silica gel column (20 1.7 cm). Elution with 100:1 hexanes/ethyl acetate gave the product as a yellow oil: yield 342 mg (94%); silica gel TLC $R_f$ 0.7 (8:1:1 hexanes/ethyl acetate/methanol); ¹H NMR ($CDCl_3$) δ 0.87 (t, 3H, J=6.8 Hz), 1.25-1.39 (m, 16H), 1.66 (quint, 2H, J=7.2 Hz), 2.17 (s, 3H), 2.77 (t, 2H, J=8.0 Hz), 2.83-2.87 (m, 5H) and 3.40 (t, 2H, J=8.0 Hz); ¹³C NMR ($CDCl_3$) δ 14.1, 19.5, 22.7, 25.2, 28.7, 29.4, 29.54, 29.59, 29.64, 29.64, 31.9, 33.0, 38.1, 52.4, 110.9, 120.4, 141.1, 156.8 and 161.8; mass spectrum, m/z 366.2 and 268.2 (M)⁺ (theoretical 366.2 and 368.2); mass spectrum (APCI), m/z 367.1747 and 369.1673 (M+H)⁺ ($C_{19}H_{32}N_2Br$ requires 367.1749 and 369.1728).

Example 8

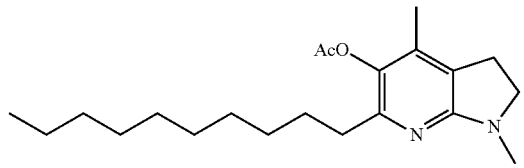 [SMILES: CCCCCCCCCCc1nc2c(c(C)c1OC(C)=O)CCN2C]

1,4-Dimethyl-6-decyl-2,3-dihydro-1H-pyrrolo[2,3-b]pyridin-5-yl acetate (2b)

To a solution of 43.0 mg (0.12 mmol) of 5-bromo-1,4-dimethyl-6-decyl-2,3-dihydro-1H-pyrrolo[2,3-b]pyridine in 1 mL of THF was added 17.4 μL (0.12 mmol) of tetramethylethylenediamine (TMEDA) at −78° C. followed by 146.3 μL (0.23 mmol, 1.6 M in hexanes) of n-BuLi. After 30 min, 28.7 μL (0.26 mmol) of trimethoxy boron was added and the resulting mixture was stirred for another 1 h. To the reaction mixture was added slowly 54.2 μL (0.26 mmol, 32 wt %) of peracetic acid and the solution was then warmed to 0° C. over a period of 30 min. The mixture was diluted by 5 mL of $H_2O$ and extracted with three 5-mL portions of EtOAc. The combined organic layer was washed with brine, dried ($MgSO_4$) and the solvent was concentrated under diminished pressure. The resulting oil was dissolved in 2 mL of $CH_2Cl_2$ at 0° C., followed by the addition of 97.9 μL (0.70 mmol) of triethylamine, 1.4 mg (0.01 mmol) of DMAP and 33.1 μL (0.35 mmol) of acetic anhydride. The reaction was stirred at room temperature for 1 h and quenched by the addition of 2 mL of sat aq $NH_4Cl$. The solution was then extracted with three 5-mL portions of EtOAc. The combined organic layer was washed with brine, dried ($MgSO_4$) and the solvent was concentrated under diminished pressure. The residue was purified by flash chromatography on a silica gel column (20 1.7 cm). Elution with 100:1 hexanes/ethyl acetate gave 2b as a yellow oil: yield 28.0 mg (68%); silica gel TLC $R_f$ 0.15 (3:7 EtOAt/hexanes); $^1H$ NMR ($CDCl_3$) δ 0.86 (t, 3H, J=6.8 Hz), 1.24-1.28 (m, 16H), 1.60 (quint, 2H, J=7.6 Hz), 1.92 (s, 3H), 2.28 (s, 3H), 2.44 (t, 2H, J=8.0 Hz), 2.82 (t, 2H, J=8.4 Hz), 2.87 (s, 3H) and 3.41 (t, 2H, J=8.4 Hz); $^{13}C$ NMR ($CDCl_3$) δ 12.9, 14.1, 20.5, 22.7, 24.6, 28.7, 29.3, 29.5, 29.6, 28.6, 31.9, 32.5, 33.3, 52.8, 120.1, 134.7, 136.5, 149.7, 161.2 and 169.9; mass spectrum, m/z 346.3 $(M)^+$ (theoretical 246.3); mass spectrum (APCI), m/z 347.2696 $(M+H)^+$ ($C_{21}H_{35}N_2O_2$ requires 347.2699).

Example 9

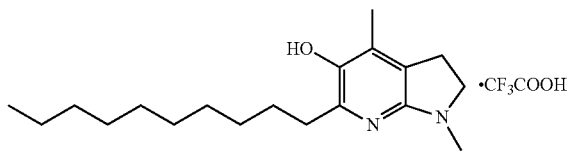 [SMILES: CCCCCCCCCCc1nc2c(c(C)c1O)CCN2C ; "·CF3COOH"]

1,4-Dimethyl-6-decyl-2,3-dihydro-1H-pyrrolo[2,3-b]pyridin-5-ol trifluoro acetic acid salt (1b)

To a solution of 19.0 mg (54.8 μmol) of 2b in 1 mL of $CH_2Cl_2$ was added 165 μL (165 μmol, 1.0 M in hexanes) of DIBAL-H at 78° C. The reaction mixture was stirred at −78° C. for 1 h and then 2 mL of sat aq sodium potassium tartrate was added slowly. The reaction mixture was slowly warmed to room temperature over a period of 30 min. The solution was extracted with three 5-mL portions of ethyl acetate. The combined organic layer was washed with brine, dried ($MgSO_4$) and concentrated under diminished pressure to give the crude product as a yellow oil: silica gel TLC $R_f$ 0.16 (1:9 MeOH/$CH_2Cl_2$). The residue was then dissolved in 1 mL of $CH_3CN$ and 1% aq TFA, frozen and lyophilized. The crude product was purified on a Prepex $C_8$ reversed phase semi-preparative (250 mm×10 mm) HPLC column using a gradient of methanol and water. Linear gradients were employed using 1:4 methanol/water→4:1 methanol/water over a period of 20 min, and then 4:1 methanol/water→methanol over a period of 40 min, at a flow rate of 3.5 mL/min (monitoring at 260 nm). Fractions containing the desired product eluted at 28.2 min, and were collected, frozen, and lyophilized to give 1b as a light yellow solid: yield 13.0 mg (76%); $^1H$ NMR ($CD_3CN$) δ 0.89 (t, 3H, J=6.8 Hz), 1.27-1.31 (m, 16H), 1.54 (quint, 2H, J=7.6 Hz), 2.13 (s, 3H), 2.70 (t, 2H, J=8.0 Hz), 2.99 (t, 2H, J=8.4 Hz), 3.06 (s, 3H) and 3.72 (t, 2H, J=8.4 Hz); $^{13}C$ NMR ($CDCl_3$) δ 13.0, 13.4, 22.4, 24.41, 27.3, 28.6, 28.9, 29.00, 29.04, 29.3, 29.3, 31.6, 32.4, 53.1, 117.3, 126.1, 132.1, 140.3, 141.5 and 152.1; mass spectrum, m/z 304.3 $(M)^+$ (theoretical 304.3); mass spectrum (APCI), m/z 305.2590 $(M+H)^+$ ($C_{19}H_{33}N_2O$ requires 305.2593).

Example 10

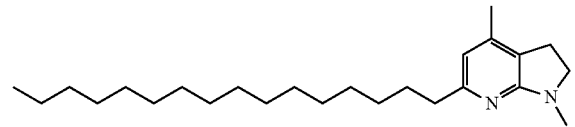 [SMILES: CCCCCCCCCCCCCCCCc1cc(C)c2c(n1)N(C)CC2]

1,4-Dimethyl-6-hexadecyl-2,3-dihydro-1H-pyrrolo[2,3-b]pyridine

To a solution of 277 mg (1.71 mmol) of 1,4,6-trimethyl-2,3-dihydro-1H-pyrrolo[2,3-b]pyridine in 5 mL of THF was added 1.71 mL (2.73 mmol, 1.6 M in hexanes) of n-BuLi followed by 518 μL (1.79 mmol) of 1-bromononane at 78° C. The reaction mixture was slowly warmed to room temperature and stirred for another 16 h. The reaction mixture was quenched by the addition of 10 mL of sat aq $NH_4Cl$ at 0° C. The mixture was extracted with EtOAc. The combined organic layer was Washed with brine, dried ($MgSO_4$) and concentrated under diminished pressure. The residue was purified by flash chromatography on a silica gel column (25 3.2 cm). Elution with 10:1 hexanes/ethyl acetate gave the product as a white solid: yield 330 mg (52%); mp 43-45° C.; silica gel TLC $R_f$ 0.25 (8:1:1 hexanes/ethyl acetate/MeOH); $^1H$ NMR ($CDCl_3$) δ 0.88 (t, 3H, J=7.2 Hz), 1.25-1.31 (m, 28H), 1.66 (quint, 2H, J=7.6 Hz), 2.08 (s, 3H), 2.55 (t, 2H, J=8.0 Hz), 2.80 (t, 2H, J=8.4 Hz), 2.90 (s, 3H), 3.38 (t, 2H, J=8.4 Hz) and 6.13 (s, 1H); $^{13}C$ NMR ($CDCl_3$) δ 14.1, 18.0, 22.7, 24.4, 29.38, 29.38, 29.57, 29.62, 29.65, 29.68, 29.72, 29.72, 29.72, 29.72, 29.72, 29.72, 30.0, 32.0, 33.2, 38.1, 52.4, 112.4, 118.2, 141.0, 159.1 and 163.7; mass spectrum, m/z 372.3 $(M^+)$ (theoretical 372.4); mass spectrum (APCI), m/z 373.3574 $(M+H)^+$ ($C_{25}H_{45}N_2$ requires 373.3583).

Example 11

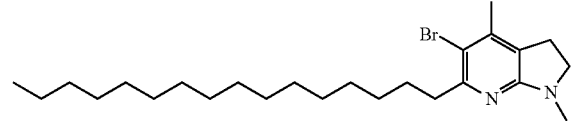 [SMILES: CCCCCCCCCCCCCCCCc1nc2c(c(C)c1Br)CCN2C]

5-Bromo-1,4-dimethyl-6-hexadecyl-2,3-dihydro-1H-pyrrolo[2,3-b]pyridine

To a solution of 278 mg (0.75 mmol) of 1,4-dimethyl-6-hexadecyl-2,3-dihydro-1H-pyrrolo[2,3-b]pyridine in 4 mL of chloroform was added 108 mg (0.38 mmol) of 1,3-dibromo-5,5-dimethylhydantoin in portions at 0° C. The reaction mixture was stirred at 0° C. for 30 min. The reaction was quenched by the addition of 5 mL of sat aq NaHCO$_3$. The mixture was extracted with chloroform and the combined organic layer was washed with brine and dried over MgSO$_4$. The concentrated residue was purified by flash chromatography on a silica gel column (20 1.7 cm). Elution with 100:1 hexanes/ethyl acetate gave the product as a white solid: yield 331 mg (98%); nip 49-50° C.; silica gel TLC R$_f$ 0.78 (8:1:1 hexanes/ethyl acetate/methanol); $^1$H NMR (CDCl$_3$) δ 0.88 (t, 3H, J=7.2 Hz), 1.25-1.31 (m, 28H), 1.66 (quint, 2H, J=7.6 Hz), 2.08 (s, 3H), 2.55 (t, 2H, j=8.0 Hz), 2.80 (t, 2H, J=8.4 Hz), 2.90 (s, 3H), 3.38 (t, 2H, J=8.0 Hz) and 6.13 (s, 1H); $^{13}$C NMR (CDCl$_3$), δ 14.1, 19.5, 22.7, 25.2, 28.7, 29.4, 29.57, 29.61, 29.65, 29.68, 29.71, 29.71, 29.71, 29.71, 29.71, 31.9, 33.0, 38.1, 52.4, 110.9, 120.3, 141.1, 156.8 and 161.8; mass spectrum, m/z 451.3 and 453.2 (M+H)$^+$ (theoretical 451.3 and 453.3); mass spectrum (APCI), m/z 451.2680 and 453.2697 (M+H)$^+$ (C$_{25}$H$_{44}$N$_2$Br requires 451.2688 and 453.2667).

Example 12

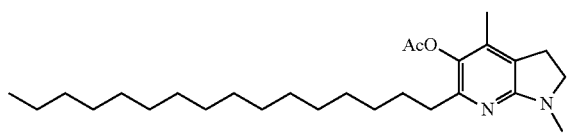 [SMILES: CCCCCCCCCCCCCCCCc1nc2c(c(C)c1OC(C)=O)CCN2C]

1,4-Dimethyl-6-hexadecyl-2,3-dihydro-1H-pyrrolo[2,3-b]pyridin-5-yl acetate (2c)

To a solution of 43.5 mg (0.10 mmol) of 5-bromo-1,4-dimethyl-6-hexadecyl-2,3-dihydro-1H-pyrrolo[2,3-b]pyridine in 1 mL of THF was added 14.2 µL (0.10 mmol) of tetramethylethylenediamine (TMEDA) at −20° C. followed by 119 µL (0.19 mmol, 1.6 M in hexanes) of n-BuLi. After 30 min, 23.4 µL (0.21 mmol) of trimethoxy boron was added and the resulting mixture was stirred for another 1 h. To the reaction mixture was added slowly 44.1 µL (0.21 mmol, 32 wt %) of peracetic acid and the solution was then warmed to 0° C. over a period of 30 min. The mixture was diluted by 5 mL of H$_2$O and extracted with three 5-mL portions of EtOAc. The combined organic layer was washed with brine, dried (MgSO$_4$) and the solvent was concentrated under diminished pressure. The resulting oil was dissolved in 2 mL of CH$_2$Cl$_2$ at 0° C., followed by the addition of 79.6 µL (0.57 mmol) of triethylamine, 1.2 mg (0.01 mmol) of DMAP and 27.0 µL (0.29 mmol) of acetic anhydride. The reaction mixture was stirred at room temperature for 1 h and quenched by the addition of 2 mL of sat aq NH$_4$Cl. The solution was then extracted with three 5-mL portions of EtOAc. The combined organic layer was washed with brine, dried (MgSO$_4$) and the solvent was concentrated under diminished pressure. The residue was purified by flash chromatography on a silica gel column (20 1.7 cm). Elution with 100:1 hexanes/ethyl acetate gave 2c as a yellow oil: yield 15.0 mg (37%); silica gel TLC R$_f$ 0.20 (3:7 EtOAt/hexanes); $^1$H NMR (CDCl$_3$) δ 0.86 (t, 3H, J=6.8 Hz), 1.23-1.28 (m, 28H), 1.60 (quint, 2H, J=7.6 Hz), 1.93 (s, 3H), 2.28 (s, 3H), 2.44 (t, 2H, J=8.0 Hz), 2.82 (t, 2H, J=8.0 Hz), 2.87 (s, 3H) and 3.41 (t, 2H, J=8.0 Hz); $^{13}$C NMR (CDCl$_3$) δ 12.9, 14.1, 20.5, 22.7, 24.6, 28.7, 29.4, 29.51, 29.59 29.64, 29.68, 29.68, 29.68, 29.68, 29.68, 29.68, 29.68, 31.9, 32.5, 33.3, 52.8, 120.1, 134.7, 136.5, 149.7, 161.2 and 169.9; mass spectrum, m/z 430.3 (M)$^+$ (theoretical 430.4); mass spectrum (APCI), m/z 431.3637 (M+H)$^+$ (C$_{27}$H$_{47}$N$_2$O$_2$ requires 431.3638).

Example 13

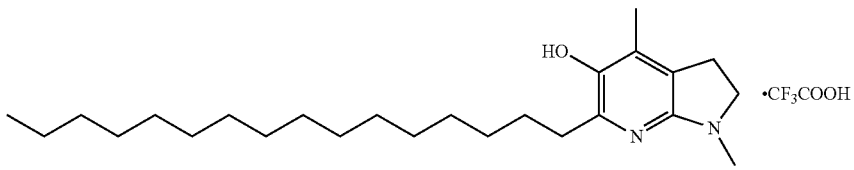 [SMILES: CCCCCCCCCCCCCCCCc1nc2c(c(C)c1O)CCN2C ; "·CF3COOH"]

1,4-Dimethyl-6-hexadecyl-2,3-dihydro-1H-pyrrolo[2,3-b]pyridin-5-ol trifluoroacetic acid salt (1c)

To a solution of 15.0 mg (34.8 µmol) of 2c in 1 mL of CH$_2$Cl$_2$ was added 105 µL (105 µmol, 1.0 M in hexanes) of DIBAL-H at 78° C. The reaction mixture was stirred at 78° C. for 1 h and then 2 mL of sat aq sodium potassium tartrate was added slowly. The reaction mixture was slowly warmed to room temperature over a period of 30 min. The solution was extracted with three 5-mL portions of ethyl acetate. The combined organic layer was washed with brine, dried (MgSO$_4$) and concentrated under diminished pressure to give the crude product as a yellow oil: silica gel TLC R$_f$ 0.22 (1:9 MeOH/CH$_2$Cl$_2$). The residue was then dissolved in 1 mL of CH$_3$CN and 1% aq TFA, frozen and lyophilized. The crude product was purified on a Prepex C$_8$ reversed phase semi-preparative (250 mm×10 mm) HPLC column using a gradient of methanol and water. Linear gradients were employed using 1:4 methanol/water→4:1 methanol/water over a period of 20 min, and then 4:1 methanol/water→methanol over a period of 40 min, at a flow rate of 3.5 mL/min (monitoring at 260 nm). Fractions containing the desired product eluted at 37.5 min, and were collected, frozen, and lyophilized to give 1c as a light yellow solid: yield 11.0 mg (82%); $^1$H NMR (CD$_3$CN) δ 0.89 (t, 3H, J=6.4 Hz), 1.27-1.36 (m, 28H), 1.55 (quint, 2H, J=7.2 Hz), 2.13 (s, 3H), 2.70 (t, 2H, J=8.0 Hz), 3.00 (t, 2H, J=8.4 Hz), 3.06 (s, 3H) and 3.73 (t, 2H, J=8.4 Hz); $^{13}$C NMR (CDCl$_3$) δ 13.0, 13.4, 22.4, 24.4, 27.2, 28.6, 28.7, 28.99, 29.06, 29.07, 29.2, 29.30, 29.33, 29.36, 29.39, 29.39, 29.39, 31.6, 32.4, 53.1, 117.3, 126.2, 131.9, 140.2, 141.4 and 152.1; mass spectrum, m/z 388.3 (M)$^+$ (theoretical 388.3); mass spectrum (APCI), m/z 389.3526 (M+H)$^+$ (C$_{25}$H$_{45}$N$_2$O requires 389.3532).

Example 14

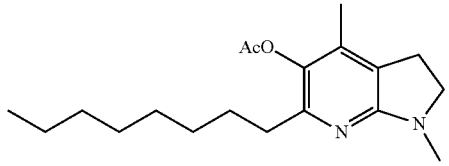 [SMILES: CCCCCCCCc1nc2c(c(C)c1OC(C)=O)CCN2C]

1,4-Dimethyl-6-octyl-2,3-dihydro-1H-pyrrolo[2,3-b]pyridin-5-yl acetate (1d)

Step 1: To a mixture containing 10 mL (10.28 g, 104 mmol) of N-methyl-2-pyrrolidinone and 10 mL (13.25 g, 105 mmol) of dimethyl sulfate was stirred and heated at 90° C. for 1.5 h, then allowed to cool to room temperature. A solution containing 25 mL of 25% methanolic sodium methoxide and 72 mL of methanol was added at −10° C. under Ar over a period of 1 h. The precipitated solid was filtered and the solvent was concentrated under diminished pressure. The residue was dissolved in 100 mL of ether and stirred for 1 h, then the precipitated solid was filtered. The solid was washed with two 10-mL portions of ether. After concentration under diminished pressure, the residue was distilled in vacuo to give 2,2-dimethoxy-1-methylpyrrolidine as a yellow liquid: yield 4.42 g (29%); $^1$H NMR (CDCl$_3$) δ 1.62-1.74 (m, 2H), 1.83 (t, 2H, J=7.8 Hz), 2.28 (s, 3H), 2.78 (t, 2H, J=6.6 Hz), 3.15 (s, 3H).

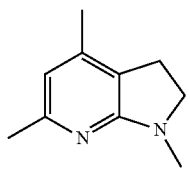

1,4,6-Trimethyl-2,3-dihydro-1H-pyrrolo[2,3-b]pyridine

Step 2: To a solution containing 1.20 g (12.1 mmol) of 4-amino-3-penten-2-one in 8 mL of toluene was added 3.00 g (20.7 mmol) of 2,2-Dimethoxy-1-methylpyrrolidine. The reaction mixture was heated at reflux and stirred for 2 h, cooled to 90° C., and then treated with 2.38 g (24.8 mmol) of t-BuONa and 2 mL of t-BuOH. The reaction mixture was stirred at 90° C. for another 16 h. The cooled reaction mixture was quenched by the addition of 10 mL of sat aq. NH$_4$Cl. The mixture was extracted with three 30-mL portions of EtOAc. The combined organic layer was washed with brine, dried over anhydrous MgSO$_4$, filtered, and concentrated under diminished pressure. The residue was purified via flash chromatography on a silica gel column (42×2.5 cm). Step gradient elution with 1:4→1:1 ethyl acetate-hexanes as eluent gave 1,4,6-trimethyl-2,3-dihydro-1H-pyrrolo[2,3-b]pyridine as a brown oil: yield 0.62 g (32%); silica gel TLC R$_f$ 0.15 (1:4 ethyl acetate-hexanes); $^1$H NMR (CDCl$_3$) 1.91 (s, 3H), 2.20 (s, 3H), 2.65 (t, 2H, J=8.4 Hz), 2.76 (s, 3H), 3.23 (t, 2H, J=8.4 Hz), 5.98 (s, 1H).

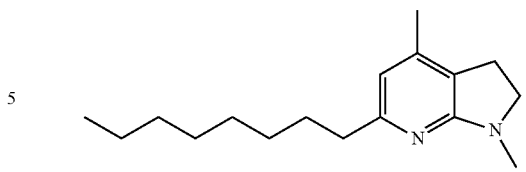

1,4-Dimethyl-6-octyl-2,3-dihydro-1H-pyrrolo[2,3-b]pyridine

Step 3: To a solution containing ~490 mg (2.71 mmol) of 1,4,6-Trimethyl-2,3-dihydro-1H-pyrrolo[2,3-b]pyridine in 7.2 mL of THF was added 2.70 mL (4.34 mmol) of n-BuLi (1.6 M in hexanes) followed by 4504 (509 mg, 2.85 mmol) of 1-bromoheptane at −78° C. The reaction mixture was slowly warmed to room temperature and stirred for 16 h. The reaction mixture was quenched by the addition of 25 mL of sat aq. NH$_4$Cl at 0° C. The mixture was extracted with three 40-mL portions, of EtOAc. The combined organic layer was washed with brine, dried over anhydrous MgSO$_4$, filtered, and concentrated under diminished pressure. The residue was purified via flash chromatography on a silica gel column (42×2.5 cm). Step gradient elution with 1:10→1:4 ethyl acetate-hexanes as eluent gave 1,4-dimethyl-6-octyl-2,3-dihydro-1H-pyrrolo[2,3-b]pyridine as a yellow oil: yield 402 mg (57%); silica gel TLC R$_f$ 0.36 (8:1:1 hexanes-ethyl acetate-methanol); $^1$H NMR (CDCl$_3$) δ 0.79 (t, 2H, J=7.2 Hz), 1.16-1.30 (m, 10H), 1.58 (quint, 2H, J=8.0 Hz), 2.00 (s, 3H), 2.48 (t, 2H, J=8.0 Hz), 2.72 (t, 2H, J=8.4 Hz), 2.82 (s, 3H), 3.38 (t, 2H, J=8.4 Hz), 6.14 (s, 1H).

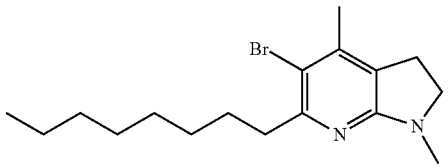 [SMILES: CCCCCCCCc1nc2c(c(C)c1Br)CCN2C]

5-Bromo-1,4-dimethyl-6-octyl-2,3-dihydro-1H-pyrrolo[2,3-b]pyridine

Step 4: To a solution containing 402 mg (1.54 mmol) of 1,4-Dimethyl-6-octyl-2,3-dihydro-1H-pyrrolo[2,3-b]pyridine in 6 mL of chloroform was added 220 mg (0.77 mmol) of 1,3-dibromo-5,5-dimethylhydantoin in five portions at 0° C. The reaction mixture was stirred at 0° C. for 30 min. The reaction mixture was quenched by the addition of 8 mL of sat aq. NaHCO$_3$. The mixture was extracted with three 25-mL portions of chloroform. The combined organic layer was washed with brine, dried over anhydrous MgSO$_4$, filtered, and concentrated under diminished pressure. The residue was purified via flash chromatography on a silica gel column (43×2.5 cm). Step gradient elution with 1:10 ethyl acetate-hexanes as eluent gave 5-bromo-1,4-dimethyl-6-octyl-2,3-dihydro-1H-pyrrolo[2,3-b]pyridine as a yellow oil: yield 371 mg (71%); silica gel TLC R$_f$ 0.65 (8:1:1 hexanes-ethyl acetate-methanol); $^1$H NMR (CDCl$_3$) δ 0.81 (t, 2H, J=7.2 Hz), 1.16-1.30 (m, 10H), 1.65 (quint, 2H, J=8.0 Hz), 2.12 (s, 3H), 2.59 (t, 2H, J=8.0 Hz), 2.79-2.85 (m, 5H), 3.41 (t, 2H, J=8.0 Hz).

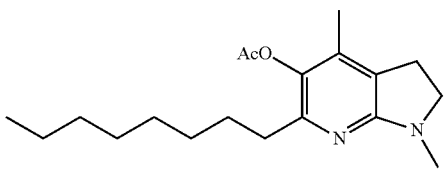 [SMILES: CCCCCCCCc1nc2c(c(C)c1OC(C)=O)CCN2C]

1,4-Dimethyl-6-octyl-2,3-dihydro-1H-pyrrolo[2,3-b]pyridin-5-yl acetate (1d)

Step 5: To a solution containing 202 mg (0.60 mmol) of 5-Bromo-1,4-dimethyl-6-octyl-2,3-dihydro-1H-pyrrolo[2,3-b]pyridine in 5 mL of THF was added 90 μL (69.7 mg, 0.60 mmol) of tetramethylethylenediamine (TMEDA) at −78° C. followed by 0.75 mL (1.20 mmol) of n-BuLi (1.6 M in hexanes). After 30 min, 147 μL (137 mg, 1.32 mmol) of trimethoxy boron was added and the resulting mixture was stirred for another 1 h. To the reaction mixture was added dropwise 277 μL (100 mg, 314 mg total solution mg, 1.32 mmol) of peracetic acid (32% wt) and the solution was then warmed to 0° C. The mixture was diluted by 20 mL of water and extracted with three 25-mL portions of EtOAc. The combined organic layer was washed with brine, dried over anhydrous MgSO$_4$, filtered, and concentrated under diminished pressure. The resulting oil was dissolved in 10 mL of CH$_2$Cl$_2$ at 0° C., followed by the addition of 485 μL (352 mg, 3.48 mmol) of triethylamine, 6.1 mg (0.05 mmol) of DMAP and 164 μL (177 mg, 1.74 mmol) of acetic anhydride. The reaction was stirred at room temperature for 1 h and quenched by the addition of 10 mL of sat aq. NH$_4$Cl. The solution was extracted with three 30-mL portions of EtOAc. The combined organic layer was washed with brine, dried over anhydrous MgSO$_4$, filtered, and concentrated under diminished pressure. The residue was purified via flash chromatography on a silica: gel column (46×2.5 cm). Step gradient elution with 1:10→1:4 ethyl acetate-hexanes as eluent gave 1d as a yellow oil: yield 92 mg (48%); silica gel TLC R$_f$ 0.22 (3:7 ethyl acetate-hexanes); $^1$H NMR (CDCl$_3$) δ 0.76 (t, 2H, J=7.2 Hz), 1.12-1.22 (m, 10H), 1.55 (quint, 2H, J=8.0 Hz), 1.88 (s, 3H), 2.20 (s, 3H), 2.35 (t, 2H, J=8.0 Hz), 2.75 (t, 2H, J=8.4 Hz), 2.88 (s, 3H), 3.42 (t, 2H, J=8.4 Hz).

Example 15

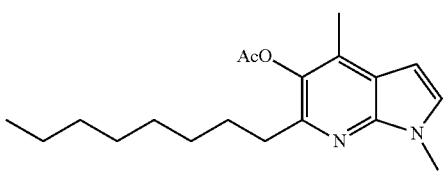 [SMILES: CCCCCCCCc1nc2c(ccn2C)c(C)c1OC(C)=O]

1,4-Dimethyl-6-octyl-1H-pyrrolo[2,3-b]pyridin-5-yl acetate (2d)

To a solution containing 65 mg (0.20 mmol) of 1d in 5 mL of benzene was added 56 mg (0.61 mmol) of nickel peroxide. The reaction was stirred at reflux for 18 h. The reaction mixture was filtered through a silica gel plug and washed with three 25-mL portions of benzene, followed by two 25-mL portions of ethyl acetate. The combined organic layer was washed with brine, dried over anhydrous MgSO$_4$, filtered, and concentrated under diminished pressure. The residue was purified via flash chromatography on a silica gel column (25×1.7 cm). Step gradient elution with 1:10→1:4 ethyl acetate-hexanes as eluent gave 1,4-dimethyl-6-octyl-1H-pyrrolo[2,3-b]pyridin-5-yl acetate (2d) as a colorless oil: yield 50 mg (48%); silica gel TLC R$_f$ 0.29 (3:7 ethyl acetate-hexanes); $^1$H NMR (CDCl$_3$) δ 0.98 (t, 3H, J=7.2 Hz), 1.35-1.50 (m, 10H), 1.72 (quint, 2H, J=8.0 Hz), 2.11 (s, 3H), 2.38 (s, 3H), 2.52 (t, 2H, J=8.0 Hz), 3.34 (s, 3H), 6.21 (d, 1H, J=3.6 Hz), 6.88 (d, 1H, J=3.6 Hz).

Example 16

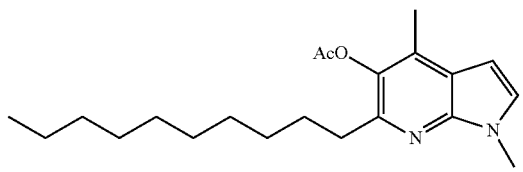 [SMILES: CCCCCCCCCCc1nc2c(ccn2C)c(C)c1OC(C)=O]

1,4-Dimethyl-6-decyl-1H-pyrrolo[2,3-b]pyridin-5-yl acetate (2e)

To a solution containing 51 mg (0.15 mmol) of 2b in 4 mL of benzene was added 42 mg (0.46 mmol) of nickel peroxide. The reaction was stirred at reflux for 18 h. The reaction mixture was filtered through a silica gel plug and washed with three 20-mL portions of benzene, followed by two 20-mL portions of ethyl acetate. The combined organic layer was washed with brine, dried over anhydrous MgSO$_4$, filtered, and concentrated under diminished pressure. The residue was purified via flash chromatography on a silica gel column (27×1.7 cm). Step gradient elution with 1:10→1:4 ethyl acetate-hexanes as eluent gave 6-decyl-1,4-dimethyl-1H-pyrrolo[2,3-b]pyridin-5-yl acetate (2e) as a colorless oil: yield 50 mg (48%); silica gel TLC R$_f$ 0.35 (3:7 ethyl acetate-hexanes); $^1$H NMR (CDCl$_3$) δ 1.05 (t, 3H, J=7.2 Hz), 1.39-1.52 (m, 14H), 1.76 (quint, 2H, J=8.0 Hz), 2.17 (s, 3H), 2.43 (s, 3H), 2.58 (t, 2H, J=8.0 Hz), 3.41 (s, 3H), 6.27 (d, 1H, J=3.6 Hz), 6.92 (d, 1H, J=3.6 Hz).

Example 17

I. Lipid Peroxidation Assay

Cis-Parinaric Acid Oxidation to Measure Lipid Peroxidation

Several methods for assaying lipid peroxidation in vitro have been developed (Kuypers et al. (1987) *Biochim Biophys Acta.* 25, 266-274; Pap et al. (1999) *FEBS Lett* 453, 278-282; Drummen et al. (2002) *Free Radic Biol Med.* 33, 473-490). Almost all of these methods are based on inhibition of free radical-induced oxidation reactions. A widely used fluorescence assay for lipid peroxidation uses lipid soluble cis-parinaric acid as a probe. cis-parinaric acid loses its fluorescence ($\lambda_{exc/em}$: 320/432 nm) upon interaction with peroxyl radicals and retains its fluorescence in the presence of radical quenchers. cis-parinaric acid is, however, air sensitive, photolabile and absorbs light in the UV region of the spectrum (at ~320 nm). However, this region of the spectrum is where most compounds have also been found to absorb and emit light. In practical terms, the results obtained using cis-parinaric as a probe for lipid peroxidation are confounded due to the overlapping of the compounds emission spectra with the cis-parinaricemission spectrum.

$C_{11}$-BODIPY$^{581/591}$ Oxidation to Measure Lipid Peroxidation

To overcome the problem of spectral overlap using cis-parinaric acid, a fluorescence assay for lipid peroxidation using a lipophilic probe belonging to the BODIPY class of fluorescent dyes was used. $C_{11}$-BODIPY$^{581/591}$ (4,4-difluoro-5(4-phenyl-1,3-butadienyl)-4-bora-3a,4a-diaza-s-indacene-3-propionic acid) fluorescence shifts from red to green upon oxidation. $C_{11}$-BODIPY$^{581/591}$ (Molecular. Probes, Eugene, Oreg., USA) stock solution concentrations were determined by measuring the absorption of $C_{11}$-BODIPY$^{581/591}$ at 582 nm using a molar extinction coefficient of 140,000 mol$^{-1}$ cm$^{-1}$ (R. P. Haugland, (1999) Handbook of Fluorescent Probes and Research Chemicals, Molecular Probes, Inc., Eugene, Oreg.). The lipid peroxidation inducer 2,2'-Azobis (2-amidino-propane dihydrochloride) (AAPH) and the antioxidant compound α-tocopherol (α-TOH) were obtained from Sigma (St. Louis, Mo., USA). Phospholipid bilayers were prepared from 1-stearoyl-2-oleoyl-phosphatidylcholine (SOPC) and 1,2-dilinoleoyl-phosphatidylcholine (DLPC) and were purchased from Avanti® polar lipids, INC (Alabaster, Ala., USA).

Preparation of Liposomes

Phosphatidylcholine (PC) liposomes were prepared as described before (Guey-Shuang et al. (1982) *Lipids*. 17, 403-413). Briefly, DLPC (25 mg) and SOPC (25 mg) were dissolved in chloroform and the solvent was removed by nitrogen evaporation (~2 hours to give a thin film of PC in a round bottom flask. The lipid film was hydrated with 50 mL of 10 mM Tris-HCl (pH 7.4), 100 mM KCl, shaken and sonicated for 15 seconds. The liposomes obtained were filtered several times through 0.2 μM membrane filter.

Measurement of $C_{11}$-BODIPY$^{581/591}$ Oxidation $C_{11}$ BODIPY$^{581/591}$ was incorporated into liposomes and oxidized by peroxyl radicals derived from the decomposition of AAPH in presence and absence of the compounds. Liposomes (1 mg/mL), suspended in 10 mM Tris-HCl (pH 7.4), 100 mM KCl, were transferred to a quartz 1 mL cuvette and placed in a Varian Cary Eclipse fluorometer (Varian, Cary, N.C.) equipped with a thermostatted cuvette holder at 40° C. Liposomes were pre-incubated for 10 min with 200 nM $C_{11}$ BODIPY$^{581/591}$ to allow their incorporation into the lipid phase of the liposomes. After the addition of AAPH (10 mM) the decay of red fluorescence was followed at λ exc=570 nm, λ em=600 nm. Relative fluorescence units were normalized to 100% intensity. Results obtained were verified by repeating experiments N=3 independent experiments.

Measurement of $C_{11}$-BODIPY$^{581/591}$ Oxidation in Cell Culture

Lipid peroxidation in CEM leukemia cells was detected by utilizing the oxidant-sensitive lipophilic probe $C_{11}$ BODIPY$^{581/591}$. Briefly, CEM cells (5×10$^5$ cell/mL) were treated with the test compounds at final concentrations of 2.5 and 5 μM, and incubated at 37° C. for 16 h in a humidified atmosphere containing 5% $CO_2$ in air. Cells were treated with 1 μM$C_{11}$ BODIPY$^{581/591}$ in phenol red-free RPMI-1640 media and incubated at 37° C. in the dark for 30 minutes. The cells were washed twice with phosphate buffered saline and oxidative stress was induced with 5 mM DEM in phenol red-free RPMI-1640 media for 90 minutes. Treated cells were collected by centrifugation at 300×g for 3 minutes and then washed twice with phosphate buffered saline. Cells were re-suspended in 250 μL of phosphate buffered saline and were analyzed by FACS (FACS Calibur flow cytometer, Becton Dickinson) to monitor the change in intensity of the $C_{11}$ BODIPY$^{581/591}$-green (oxidized) fluorescence signal. A total of 10000 events were recorded for each sample and analyzed with the CellQuest software (BD Biosciences). The results were verified by repeating the experiments in duplicate. Results are expressed as the relative percentage of treated control (DEM).

Assay for Thiobarbituric Acid Reactive Species (TBARS)

Lipid peroxidation by hydrogen peroxide in bovine heart mitochondrial membranes was determined by measuring the amount of thiobarbituric acid reactive substances released. Bovine heart mitochondria (1 mg protein) prepared as described by Smith (38) were added to 800 pt of 50 mM phosphate buffer, pH 8.0, and subjected to oxidative stress by the addition of 25 in M glucose and 1 U/mL glucose oxidase from *Aspergillus niger*. Samples were incubated with or without test compounds at 37° C. for 30 minutes. Two hundred μL each of 1% (w/v) thiobarbituric acid and 35% (v/v) perchloric acid, as well as 0.1% (w/v) butylated hydroxytoluene (from a 2% stock solution in DMSO) were added. Samples were heated at 100° C. for 15 minutes. One-mL aliquots of each sample were taken and diluted in 2 mL of water, then extracted once with 2 mL of n-butanol. Triplicate 500-μL aliquots were taken from the butanol phase and transferred to a quartz cuvette. TBARS were determined fluorometrically from the emission spectrum ($\lambda_{ex}$ 515 nm; $\lambda_{em}$ 550 nm) using a Varian fluorimeter. The malondialdehyde concentration was determined based on a standard curve created using serial dilutions of 10 mM 1,1,3,3-tetraethoxypropane hydrolyzed in 1% (v/v) $H_2SO_4$ at 4° C. overnight. The malondialdehyde concentration was expressed as nmolesmanoldialdehyde per mg protein. Protein in aliquots of the homogenates was determined by the bicinchoninic acid method.

II. Reactive Oxygen Species (ROS) Assay

Cellular ROS production can be monitored using 2',7'-dichlorodihydrofluorescein diacetate (DCFH-DA) (LeBel et al. (1992) *Chem. Res. Toxicol.* 5, 227-231) (Molecular Probes, Eugene, Oreg., USA), a membrane permeable and oxidant-sensitive fluorescent dye. DCFH-DA is a non-fluorescent derivative of fluorescein that emits fluorescence after being oxidized by hydrogen peroxide and other ROS. The emitted fluorescence is directly proportional to the concentration of hydrogen peroxide. DCFH-DA is nonionic and nonpolar and is easily taken up by cells. Once inside the cell, DCFH-DA is hydrolyzed by cellular esterases to non-fluorescent DCFH which traps the dye in the cell. In the presence of ROS including hydrogen peroxide, DCFH is oxidized to the highly fluorescent compound dichlorofluorescein (DCF). The intracellular DCF fluorescence is used as an index of cellular ROS production.

Cellular oxidative stress was induced by pharmacological depletion of glutathione (GSH) using the chemical diethylmaleate (DEM). ROS production was assessed by monitoring DCF fluorescence. Leukemic CEM cells (ATCC®, catalogue number CRL-2264) were cultured in RPMI (GIBCO, Grand island, NY, USA) with 10% FCS, 2 mM glutamine (HyClone, South Logan, Utah, USA) and 1% penicillin-streptomycin mix antibiotics (Cellgro, Manassas, Va., USA) supplements. CEM cells (5×10$^5$ cell/mL) were plated (1 mL) in 24-well plate and treated with the invention compounds (final concentration 1, 2.5, and 5 μM), and incubated at 37° C., 5% $CO_2$ for 16 hours. The compounds tested were prepared by first making stock solutions (2.5 mM) in dimethylsulfoxide (DMSO). Cells were treated with 5 mM DEM for 50 minutes and collected by centrifugation at 300×g for 3 min and then washed twice with Hanks' Balanced Salt Solution (HSSB) buffer (Sigma, St. Louis, Mo. USA). Cells were re-suspended in HSSB buffer+20 mM glucose and incubated at 37° C. in the dark for 20 min with 10 μM DCFH-DA. Cells were collected by centrifugation at 300×g for 3 min and then washed twice with HSSB buffer. The samples were analyzed immediately by flow cytometry (Becton-Dickinson FACS Caliber), (Cell Quest software, BD Biosciences) using 488 nm excitation laser and FL1-H channel 538 nm emission filter. In each analysis, 10,000 events were recorded after cell debris were electronically gated out. Results obtained were verified by repeating experiments N=3 independent experiments. Authentic hydrogen peroxide was used as a positive control.

III. Mitochondrial Membrane Potential ($\Delta\psi_m$) Assay

Measurement of Mitochondrial Membrane Potential ($\Delta\psi_m$) (FACS). For the determination of $\Delta\psi_m$, CEM leukemia cells were pre-treated with or without the test compounds for 16 h. The cells were treated with 5 mM DEM for 120 minutes, collected by centrifugation at 300×g for 3 minutes and then washed twice with phosphate buffered saline. The cells were re-suspended in HSSB buffer and incubated at 37° C. in the dark for 15 minutes with 250 nM TMRM (a cationic dye which accumulates within mitochondria in accordance with the $\Delta\psi_m$ Nernst potential). Cells were collected by centrifugation at 300×g for 3 minutes and then washed twice with phosphate buffered saline. The samples were analyzed immediately by flow cytometry using 488 nm excitation laser and the FL2-H channel. The results obtained were verified in three independent experiments. The protonophore FCCP (10 μM) was used to dissipate the chemiosmotic proton gradient ($4H^+$) and served as a control for loss of $\Delta\psi_m$. In each analysis, 10,000 events were recorded and the percentage of cells exhibiting a high level of TMRM uptake, which reflects normal mitochondrial membrane potential ($\Delta\psi_m$), was determined and analyzed with the CellQuest software (BD Biosciences). The results were verified by repeating the experiments in duplicate.

IV. Trypan Blue Cell Viability Assay

Cell viability determined by trypan blue exclusion assay: This technique was used to assess the cytoprotective effects of the invention compounds in cultured cells pharmacologically treated to induce cell death by GSH depletion. DEM was used to deplete cellular GSH and induce oxidative stress. The viability of DEM-treated CEM cells was determined by their ability to exclude the dye trypan blue. Viable cells exclude trypan blue; whereas, non-viable cells take up the dye and stain blue. Briefly, CEM lymphoblasts (CCL-119) were grown in RPMI 1640 medium (GIBCO, Grand island, NY, USA) supplemented with 10% fetal calf serum, 2 mM glutamine (HyClone, South Logan, Utah, USA), 1% penicillin-streptomycin mix (Cellgro, Manassas, Va., USA). Cells were seeded at a density of $5\times10^5$ cells/mL and treated with different concentrations of the invention compounds. Cells were incubated at 37° C. in a humidified atmosphere of 5% $CO_2$ in air for 16 hours. After pre-incubation, the cells were treated with 5 mM DEM for 5.5 h. Cell viability was determined by staining cells with 0.4% trypan blue using a hemacytometer. At least 500 cells were counted for each experimental group. At the time of assay, >80% of DEM-treated cells were trypan blue positive; whereas, in non-DEM treated control cell cultures>95% cells were viable. Cell viability was expressed as the percentage of control. Data are expressed as means±S.E.M (n=3).

V. Cell Viability Assays (FACS)

Cell viability and cytotoxicity were determined by simultaneous staining live and dead cells using a two-color fluorescence assay, the Live/Dead® Viability/Cytotoxicity Kit (Molecular Probes). This assay is used to measure two recognized parameters of cell viability, intracellular esterase activity and plasma integrity. The membrane-impermeant DNA dye ethidium homodimer-1 (EthD-1) was used to identify dead cells whose plasma membrane integrity was disrupted. The membrane-permeant dye calcein-AM was used to label live cells. It penetrates into the cells where it is metabolized by cytoplasmic esterases and becomes a fluorescent but membrane-impermeant probe which is retained in viable cells. Human CEM leukemia cells were incubated overnight in RPMI medium (control) and in the presence of test compound and then treated with DEM for 3 hours. Cells were stained with 0.2 μM calcein-AM and 0.4 μM EthD-1. After 15 minutes, flow cytometry analysis was carried out using excitation at 488 nm. The green-fluorescent (539 nm) FL1-H channel, live-cell population appears in the lower right quadrant and the red-fluorescent (585 nm) FL2-H channel dead-cell population appears in the upper left quadrant (FIG. 11). In each analysis, 10,000 events were recorded. Results obtained were verified in three independent experiments.

Results

Increased DCF fluorescence in CEM cells depleted of glutathione is analyzed by flow cytometry. FIG. 1 shows representative DCF overlay of FACS histograms of CEM cells stained with DCFH-DA and analyzed as described in the experimental section. DEM treatment caused the DCF fluorescence (FL1-H) to shift right on the x-axis of the FACS histogram, indicating increased ROS production as a result of glutathione depletion. Pretreatment of CEM cells with the α-tocopherol with compound 1b and 2b afforded significantly better protection than α-tocopherol, while 1a and 2a afforded reduced protection and 1c and 2c gave intermediate protection. The results clearly show a significant decrease in the intensity of DCF fluorescence in a dose-dependent manner for the analogues having a simple aliphatic side chain with 10 carbon atoms (compounds 1b and 2b). While the shorter side chain having a five-carbon length (compounds 1a and 2a) showed reduced protection against ROS, the analogues having a linear 16-carbon side chain afforded protection almost comparable to that of α-TOH itself.

Figure 2:
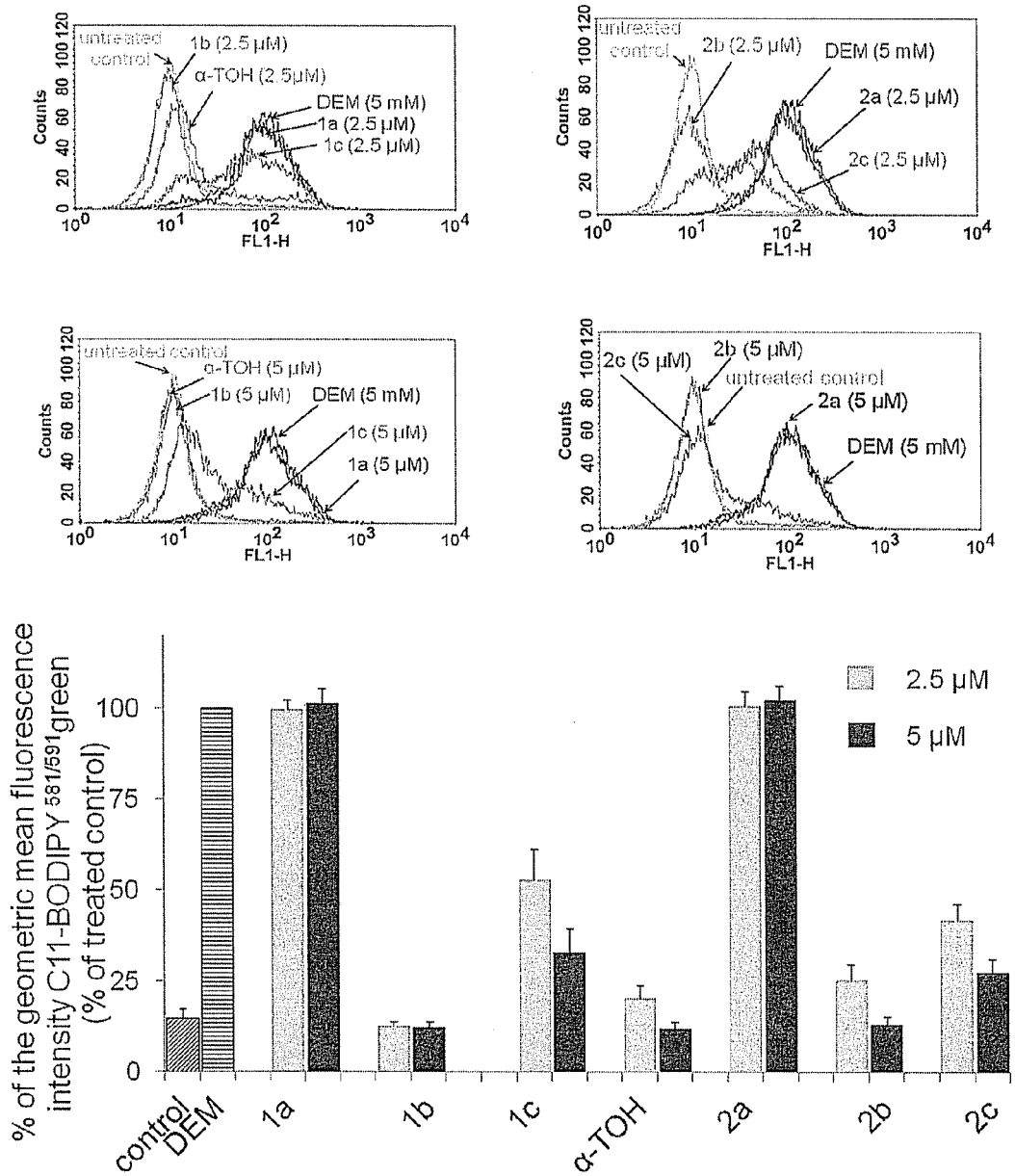
FIG. 2. Comparison of the lipid peroxidation in CEM leukemia cells depleted of glutathione detected by utilizing the oxidation-sensitive fatty acid probe $C_{-11}$ BODIPY$^{581/591}$ using flow cytometry. Increased $C_{-11}$ BODIPY-green fluorescence (oxidized form), a measure of intracellular lipid peroxidation, was determined by increasing the geometric mean fluorescence intensity (GMFI) of $C_{-11}$ BODIPY-green relative to the untreated control. A bar graph representing the percentage of the geometric mean fluorescence intensity (GMFI) of C-11 BODIPY-green fluorescence relative to a treated control is shown. Data are expressed as the mean±SEM (n=3). α-TOH is α-tocopherol.

FIG. 2 shows representative $C_{11}$-BODIPY$^{581/591}$—green (oxidized) FACS histograms overlay of CEM leukemia cells stained with BODIPY$^{581/591}$—red (reduced) and analyzed using the FL1-H channel, as described in the experimental section. DEM treatment caused the BODIPY$^{581/591}$—green fluorescence to shift right on the x-axis of the FACS histogram, indicating increased membrane peroxidation as a result of glutathione depletion. Pretreatment of CEM cells with 1b afforded significantly better protection than was achieved with α-tocopherol, while 2b gave results comparable to α-TOH. Reduced protection was observed for compounds 1c and 2c, and no protection was obtained using compounds 1a and 2a. These findings indicate the importance of side chain length, where a simple 10 carbon side chain acts as an excellent anchor to membranes and produces more efficient protection than α-TOH.

Figure 3:
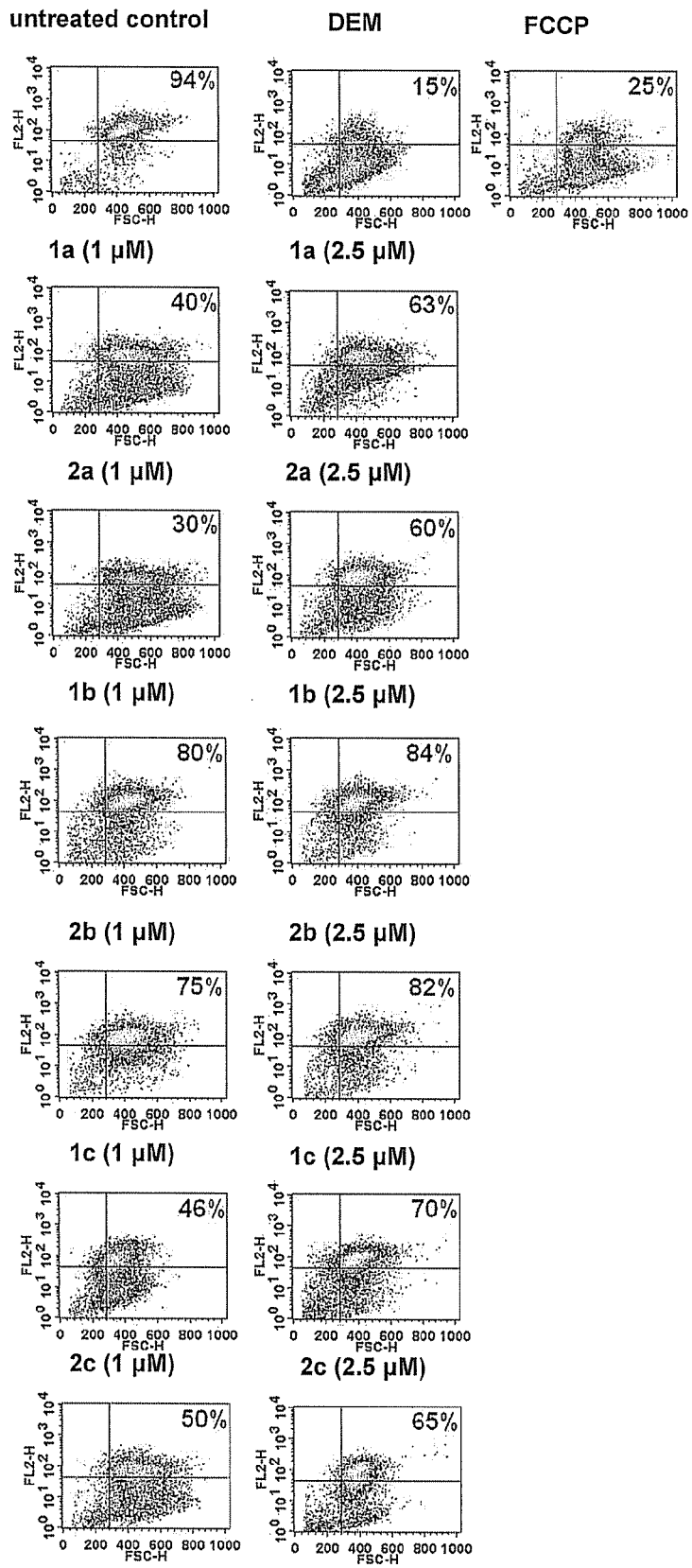
FIG. 3. Representative flow cytometric two-dimensional color density dot plot analyses of mitochondrial membrane potential ($\Delta\Psi_m$) in leukemia CEM cells stained with 250 nM TMRM and analyzed using FL2-H channel as described in the experimental section. The percentage of cells with intact $\Delta\Psi_m$ is indicated in the top right quadrant of captions. Representative example from at least three independent experiments. A total of 10000 events were recorded for each sample and analyzed with the CellQuest software (BD Biosciences).
Figure 4:
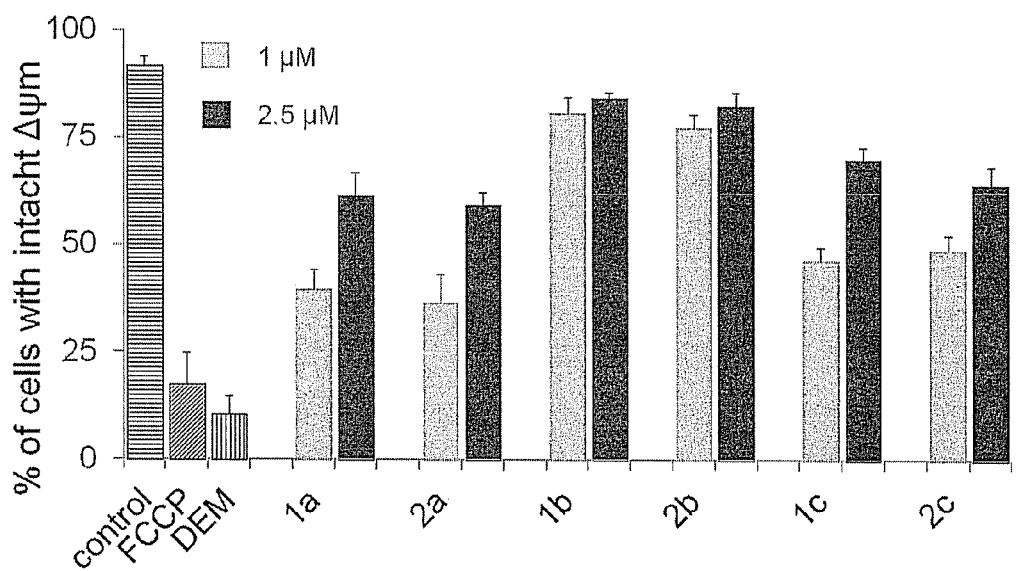
FIG. 4. A bar graph representation of means the percentage of cells with intact $\Delta\Psi_m$ recorded by FACS. Data are expressed as means±SEM of three independent experiments run in duplicate.

FIG. 3 illustrates representative two-dimensional density dot plots of TMRM-stained cells showing the percentage of cells with intact $\Delta\psi_m$ (TMRM fluorescence in top right quadrant) vs the percentage of cells with depolarized $\Delta\psi_m$ (TMRM fluorescence in bottom left and right quadrants). FIG. 4 shows a bar graph of the percentage (mean±S.E.) of CEM cells with intact $\Delta\psi_m$. The results show that DEM treatment reduced the percentage of cells with TMRM fluorescence in the top right quadrant, indicating that DEM treatment caused loss of $\Delta\psi_m$. Pretreatment of the cells for 16 hours (top panel, FIG. 3) with RPMI medium (untreated control), compounds 1a-1c and 2a-2c prevented the loss of $\Delta\psi$m induced by DEM. Once again $\Delta\psi_m$ protection was dose-dependent and compound 1b and 2b were the most effective in preventing mitochondrial depolarization, consistent with the ROS and lipid peroxidation results. Again, the analogues with shorter side chains (1a and 2a) and longer side chains (1c and 2c) were less effective in preventing mitochondrial depolarization under oxidative stress.

Figure 5:
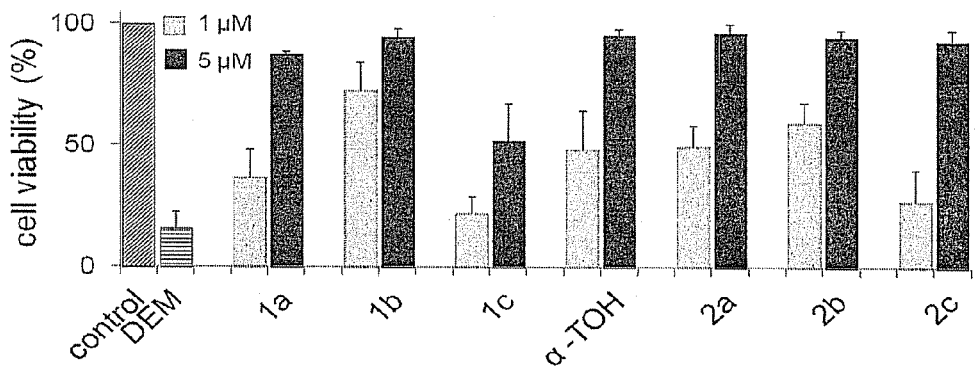
FIG. 5. Trypan blue exclusion assay of CEM cells treated with test compounds for 16 h before exposure to 5 mM diethyl maleate for 5.5 h. At the time of assay, >80% of the DEM-treated cells were trypan blue positive, whereas in the non-DEM treated control, >95% of the cells were viable. Cell viability was expressed as the percentage of control. Results are an average of three independents trials. α-TOH is α-tocopherol.

The effect of the test compounds on the viability of DEM-treated CEM leukemia cells was assessed by the trypan blue exclusion method, as presented in FIG. 5. Glutathione depletion caused significant reduction of cell viability after 5.5 h. of DEM treatment. Pretreatment of cells with α-tocopherol and the pyridinol based analogues significantly reduced cell death. Compound 1b and 2b were more effective in cytoprotection than was α-TOH (FIG. 5). With the exception of 1c, all of the analogues afforded significant cytoprotection at 5 µM concentration, and varying levels of protection when used at 1 µM concentration.

The results of this study strongly suggest that the antioxidant efficiency of α-tocopherol can be improved by designing simple synthetic α-tocopherol analogues that possess a simpler side chain than α-TOH and a pyridinol-based redox core. The best derivative among those investigated in the present study were those having a 10-carbon linear side chain (1b and 2b).

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A compound of formula:

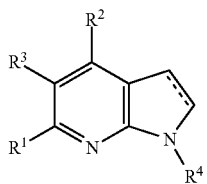

or a pharmaceutically acceptable salt thereof, wherein
bond "----" is a single or a double bond;
$R^1$ is $C_{10}$-$C_{20}$ alkyl optionally substituted with one to four substituents selected from halogen, cyano, nitro, $C_1$-$C_6$ alkyl, halo($C_1$-$C_6$ alkyl), cycloalkyl, aryl, heteroaryl, and heterocycle, wherein each cycloalkyl, aryl, heteroaryl, and heterocycle are optionally substituted with $R^9$;
wherein each $R^9$ independently is halogen, cyano, nitro, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;
$R^2$ is $C_1$-$C_4$ alkyl, $C_2$-$C_4$ alkenyl, or $C_2$-$C_4$ alkynyl;
$R^3$ is —$OR^7$, where $R^7$ is hydrogen, $C_1$-$C_6$ alkyl, halo($C_1$-$C_6$ alkyl), or —CO($C_1$-$C_6$ alkyl); and
$R^4$ is hydrogen or $C_1$-$C_6$ alkyl.

2. A compound according to claim 1, of formula:

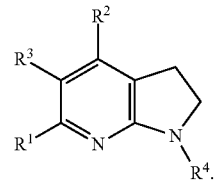

3. A compound according to claim 1, of formula:

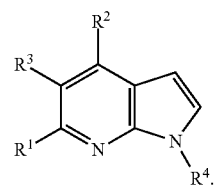

4. A compound according to claim 2, wherein $R^4$ is hydrogen or $C_1$-$C_3$ alkyl.

5. A compound according to claim 4, wherein $R^4$ is $C_1$-$C_3$ alkyl.

6. A compound according to claim 5, wherein $R^4$ is methyl or ethyl.

7. A compound according to claim 1, wherein $R^2$ is $C_1$-$C_4$ alkyl.

8. A compound according to claim 7, wherein $R^2$ is unsubstituted $C_1$-$C_2$ alkyl.

9. A compound according to claim 1, wherein $R^7$ is hydrogen, $C_1$-$C_6$ alkyl, or —CO($C_1$-$C_6$ alkyl).

10. A compound according to claim 9, wherein $R^3$ is —OH, —O($CH_3$), —OCO($C_1$-$C_6$ alkyl), or —OCOCH$_3$.

11. A compound according to claim 1, wherein $R^1$ is $C_{10}$-$C_{20}$ alkyl, optionally substituted with one to four substituents selected from halogen, cyano, nitro, $C_1$-$C_6$ alkyl, and halo($C_1$-$C_6$ alkyl).

12. A compound according to claim 11, wherein $R^1$ is $C_{10}$-$C_{20}$ alkyl, optionally substituted with one to four substituents selected from halogen, and $C_1$-$C_6$ alkyl, halo($C_1$-$C_6$ alkyl).

13. A compound according to claim 12, wherein $R^1$ is unsubstituted $C_{10}$-$C_{20}$ alkyl, straight-chain unsubstituted $C_{10}$-$C_{20}$ alkyl, decyl or hexadecyl.

14. A compound according to claim 1, wherein
$R^1$ is $C_{10}$-$C_{20}$ alkyl, optionally substituted with one to four substituents selected from halogen, cyano, nitro, $C_1$-$C_6$ alkyl, and halo($C_1$-$C_6$ alkyl);
$R^2$ is $C_1$-$C_4$ alkyl, $C_2$-$C_4$ alkenyl, or $C_2$-$C_4$ alkynyl;
$R^3$ is —$OR^7$, where $R^7$ is hydrogen, $C_1$-$C_6$ alkyl, halo ($C_1$-$C_6$ alkyl), or —CO($C_1$-$C_6$ alkyl); and
$R^4$ is hydrogen, or $C_1$-$C_6$ alkyl.

15. A compound according to claim 1, wherein $R^1$ is $C_{10}$-$C_{20}$ alkyl optionally substituted with one to four substituents selected from halogen, cyano, nitro, $C_1$-$C_6$ alkyl, and halo($C_1$-$C_6$alkyl);

$R^2$ is $C_1$-$C_4$ alkyl;

$R^3$ is —$OR^7$, where $R^7$ is hydrogen, $C_1$-$C_6$ alkyl, halo($C_1$-$C_6$ alkyl), or —CO($C_1$-$C_6$ alkyl); and $R^4$ is hydrogen, or $C_1$-$C_6$ alkyl.

16. A compound according to claim 15, wherein $R^1$ is $C_{10}$-$C_{20}$ alkyl optionally substituted with one to four substituents selected from halogen, cyano, nitro, $C_1$-$C_6$ alkyl, and halo($C_1$-$C_6$ alkyl);

$R^2$ is $C_1$-$C_4$ alkyl;

$R^3$ is —$OR^7$, where $R^7$ is hydrogen, $C_1$-$C_6$ alkyl, halo($C_1$-$C_6$ alkyl), or —CO($C_1$-$C_6$ alkyl); and $R^4$ is $C_1$-$C_6$ alkyl.

17. A compound according to claim 1, wherein $R^1$ is $C_{10}$-$C_{20}$ alkyl, optionally substituted with one to four substituents selected from halogen, cyano, nitro, $C_1$-$C_6$ alkyl, and halo($C_1$-$C_6$ alkyl);

$R^2$ is $C_1$-$C_4$ alkyl;

$R^3$ is —$OR^7$, where $R^7$ is hydrogen, $C_1$-$C_6$ alkyl, halo($C_1$-$C_6$ alkyl), or —CO($C_1$-$C_6$ alkyl); and $R^4$ is hydrogen, or $C_1$-$C_6$ alkyl.

18. A compound according to claim 17, wherein $R^1$ is $C_{10}$-$C_{20}$ alkyl;

$R^2$ is $C_1$-$C_4$ alkyl;

$R^3$ is —$OR^7$, where $R^7$ is hydrogen, $C_1$-$C_6$ alkyl, halo($C_1$-$C_6$ alkyl), or —CO($C_1$-$C_6$ alkyl); and $R^4$ is $C_1$-$C_6$ alkyl.

19. A compound, which is:

1,4-Dimethyl-6-decyl-2,3-dihydro-1H-pyrrolo[2,3-b]pyridine;

1,4-Dimethyl-6-decyl-2,3-dihydro-1H-pyrrolo[2,3-b]pyridin-5-yl acetate;

1,4-Dimethyl-6-decyl-2,3-dihydro-1H-pyrrolo[2,3-b]pyridin-5-ol;

1,4-Dimethyl-6-hexadecyl-2,3-dihydro-1H-pyrrolo[2,3-b]pyridine;

1,4-Dimethyl-6-hexadecyl-2,3-dihydro-1H-pyrrolo[2,3-b]pyridin-5-yl acetate;

1,4-Dimethyl-6-hexadecyl-2,3-dihydro-1H-pyrrolo[2,3-b]pyridin-5-ol;

or pharmaceutically acceptable salt thereof.

20. A pharmaceutical composition comprising a compound or a pharmaceutically acceptable salt according to claim 1 and an acceptable carrier, excipient and/or diluent.

21. A pharmaceutical composition comprising a compound or a pharmaceutically acceptable salt according to claim 19 and an acceptable carrier, excipient and/or diluent.

* * * * *